United States Patent
Chang et al.

(10) Patent No.: US 9,518,115 B2
(45) Date of Patent: *Dec. 13, 2016

(54) HUMANIZED ANTI-CD22 ANTIBODY

(71) Applicant: Immunomedics, Inc., Morris Plains, NJ (US)

(72) Inventors: Chien-Hsing Chang, Downingtown, PA (US); David M. Goldenberg, Mendham, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/824,751

(22) Filed: Aug. 12, 2015

(65) Prior Publication Data

US 2015/0344573 A1  Dec. 3, 2015

Related U.S. Application Data

(63) Continuation of application No. 14/603,011, filed on Jan. 22, 2015, now Pat. No. 9,139,649.

(60) Provisional application No. 61/944,295, filed on Feb. 25, 2014.

(51) Int. Cl.
| | | |
|---|---|---|
| C07K 16/00 | (2006.01) | |
| C12P 21/08 | (2006.01) | |
| A61K 39/40 | (2006.01) | |
| A61K 39/395 | (2006.01) | |
| C07K 16/28 | (2006.01) | |
| A61K 47/48 | (2006.01) | |
| A61K 45/06 | (2006.01) | |
| A61K 51/10 | (2006.01) | |
| C07K 1/00 | (2006.01) | |
| A61K 39/00 | (2006.01) | |

(52) U.S. Cl.
CPC ....... *C07K 16/2803* (2013.01); *A61K 39/3955* (2013.01); *A61K 45/06* (2013.01); *A61K 47/4863* (2013.01); *A61K 47/48384* (2013.01); *A61K 47/48407* (2013.01); *A61K 47/48561* (2013.01); *A61K 51/1027* (2013.01); *A61K 51/1069* (2013.01); *C07K 16/2851* (2013.01); *A61K 2039/505* (2013.01); *A61K 2039/507* (2013.01); *C07K 2317/24* (2013.01); *C07K 2317/31* (2013.01); *C07K 2317/54* (2013.01); *C07K 2317/565* (2013.01); *C07K 2317/567* (2013.01); *C07K 2317/569* (2013.01); *C07K 2317/622* (2013.01); *C07K 2317/73* (2013.01)

(58) Field of Classification Search
None
See application file for complete search history.

(56) References Cited

U.S. PATENT DOCUMENTS

| | | |
|---|---|---|
| 5,484,892 A | 1/1996 | Tedder et al. |
| 5,593,676 A | 1/1997 | Bhat et al. |
| 5,679,640 A | 10/1997 | Gaeta et al. |
| 5,686,072 A | 11/1997 | Uhr et al. |
| 5,736,137 A | 4/1998 | Anderson et al. |
| 5,750,105 A | 5/1998 | Newman et al. |
| 5,776,093 A | 7/1998 | Goldenberg |
| 5,776,456 A | 7/1998 | Anderson et al. |
| 5,789,554 A | 8/1998 | Leung et al. |
| 5,795,967 A | 8/1998 | Aggarwal et al. |
| 6,051,228 A | 4/2000 | Aruffo et al. |
| 6,090,365 A | 7/2000 | Kaminski |
| 6,183,744 B1 | 2/2001 | Goldenberg et al. |
| 6,187,287 B1 | 2/2001 | Leung et al. |
| 6,254,868 B1 | 7/2001 | Leung et al. |
| 6,306,393 B1 | 10/2001 | Goldenberg et al. |
| 6,846,476 B2 | 1/2005 | White |
| 7,074,403 B1 | 7/2006 | Goldenberg et al. |
| 7,321,026 B2 | 1/2008 | Leung et al. |
| 7,338,659 B2 | 3/2008 | Leung et al. |
| 7,491,514 B2 | 2/2009 | Leung et al. |
| 7,495,081 B2 | 2/2009 | Leung et al. |
| 7,521,056 B2 | 4/2009 | Chang et al. |

(Continued)

FOREIGN PATENT DOCUMENTS

| | | |
|---|---|---|
| CN | 103214578 | 7/2013 |
| EP | 0332865 | 2/1989 |
| WO | 91/09967 | 7/1991 |
| WO | 91/11465 | 8/1991 |
| WO | 91/13974 | 9/1991 |
| WO | 92/22653 | 12/1992 |
| WO | 93/19668 A1 | 10/1993 |
| WO | 94/09136 | 4/1994 |
| WO | 94/27638 | 12/1994 |
| WO | 98/04281 | 2/1998 |

(Continued)

OTHER PUBLICATIONS

Amit et al Science vol. 233 747-753 1986.*

(Continued)

*Primary Examiner* — Chun Dahle
(74) *Attorney, Agent, or Firm* — Richard A. Nakashima

(57) ABSTRACT

Disclosed are humanized RFB4 antibodies or antigen-binding fragments thereof. therapy of B-cell associated diseases, such as B-cell malignancies, autoimmune disease and immune dysfunction disease. Preferably, hRFB4 comprises the light and heavy chain RFB4 CDR sequences with human antibody FR and constant region sequences, along with heavy chain framework region (FR) amino acid residues Q1, F27, V48, A49, F68, R98, T117 and light chain residues L4, S22, K39, G100, V104, and K107. More preferably, the heavy and light chain variable region sequences of hRFB4 comprise SEQ ID NO:7 and SEQ ID NO:8, respectively. In certain embodiments, trogocytosis (antigen shaving) induced by hRFB4 plays a significant role in determining antibody efficacy and disease responsiveness for treatment of B-cell diseases, such as hematopoietic cancers, immune system dysfunction and/or autoimmune disease.

25 Claims, 11 Drawing Sheets

(56) References Cited

U.S. PATENT DOCUMENTS

| | | |
|---|---|---|
| 7,527,787 B2 | 5/2009 | Chang et al. |
| 7,534,866 B2 | 5/2009 | Chang et al. |
| 7,550,143 B2 | 6/2009 | Chang et al. |
| 7,641,901 B2 | 1/2010 | Goldenberg et al. |
| 7,666,400 B2 | 2/2010 | Chang et al. |
| 7,772,373 B2 | 8/2010 | Hansen et al. |
| 7,820,161 B1 | 10/2010 | Curd et al. |
| 7,837,995 B2 | 11/2010 | Goldenberg et al. |
| 7,910,103 B2 | 3/2011 | Goldenberg |
| 7,931,903 B2 | 4/2011 | Hansen et al. |
| 7,939,073 B2 | 5/2011 | Goldenberg et al. |
| 8,105,596 B2 | 1/2012 | Goldenberg et al. |
| 8,420,086 B2 | 4/2013 | Govindan et al. |
| 8,771,694 B2 | 7/2014 | Leung et al. |
| 9,139,649 B2 * | 9/2015 | Chang .............. C07K 16/2803 |
| 2003/0040606 A1 | 2/2003 | Leung et al. |
| 2005/0033028 A1 | 2/2005 | Leung et al. |
| 2005/0118182 A1 | 6/2005 | Pastan et al. |
| 2006/0194276 A1 | 8/2006 | Krauss et al. |
| 2007/0298035 A1 | 12/2007 | Leung et al. |
| 2008/0182975 A1 | 7/2008 | Leung et al. |
| 2008/0227957 A1 | 9/2008 | Leung et al. |
| 2010/0034738 A1 | 2/2010 | Goldenberg et al. |
| 2010/0197896 A1 | 8/2010 | Leung et al. |
| 2013/0142787 A1 | 6/2013 | Chang et al. |
| 2014/0212425 A1 | 7/2014 | Chang et al. |

FOREIGN PATENT DOCUMENTS

| | | |
|---|---|---|
| WO | 98/50435 | 11/1998 |
| WO | 99/54440 | 10/1999 |
| WO | 00/67795 A1 | 11/2000 |
| WO | 00/67796 | 11/2000 |
| WO | 00/74718 A1 | 12/2000 |
| WO | 2013/188864 | 12/2013 |

OTHER PUBLICATIONS

MacCallum et al. J. Mol. Biol. (1996) 262, 732-745.*
Pascalis et al. The Journal of Immunology (2002) 169, 3076-3084.*
Vajdos et al. JMB (2002) 320, 415-428.*
Abdel-Raheem et al., "Severe Evan's syndrome secondary to interleukin-2 therapy: treatment with chimeric monoclonal anti-CD20 antibody", Annals of hematology (2001) 80:9 543-545.
Aozasa, K. et al., "The Occurrence of Monocytoid B-lymphocytes in Autoimmune Disorders", Mod. Pathol., 6(2): 121-124, 1993.
Bendig, "Humanization of rodent monoclonal antibodies by CDR grafting", Methods: A Companion to Methods in Enzymology 8:83-93 (1995).
Brozek, C. M. et al., "Anti-DR antibodies inhibit in vitro production of human rheumatoid factor", J. Clin. Lab. Immunol., 31(3): 105-109, 1990.
Carnahan et al., "Epratuzumab, a CD22-targeting recombinant humanized antibody with a different mode of action from rituximab", Mol Immunol. Feb. 2007;44(6):1331-41.
Carvello et al., "Inotuzumab ozogamicin murine analog-mediated B-cell depletion reduces anti-islet allo- and autoimmune responses", Diabetes. Jan. 2012;61(1):155-65.
Chevallier et al., "BCR-ABL1 molecular remission after 90Y-epratuzumab tetraxetan radioimmunotherapy in CD22+Ph+B-ALL: proof of principle", Eur J Haematol. Dec. 2013;91(6):552-6.
Datta et al., "Expression of MHC class II-associated invariant chain (Ii;CD74) in thymic epithelial neoplasms", Appl. Immunohistochem Mol. Morphol. 8(3):210-215, (2000).
Dorner et al., "Targeting CD22 as a strategy for treating systemic autoimmune diseases", Ther Clin Risk Manag. Oct. 2007;3(5):953-9.
Dorner et al., "Targeting B cells in immune-mediated inflammatory disease: a comprehensive review of mechanisms of action and identification of biomarkers", Pharmacol Ther. Mar. 2010;125(3):464-75.

Ellis et al., "Engineered anti-CD38 monoclonal antibodies for immunotherapy of multiple myeloma", Journal of Immunol. 155:925-937.
Gondo et al., "HLA class II antigen associated invariant chain gene expression in malignant lymphoma", British J. of Haematology 67:413-417 (1987).
Goodkin et al., "Low-Dose (7.5 mg) Oral Methotrexate Reduces the Rate of Progression in Chronic Progressive Multiple Sclerosis", Ann Neurol 1995;37:30-40.
Govindan et al., "Radionuclides Linked to a CD74 Antibody as Therapeutic Agents for B-Cell Lymphoma: Comparison of Auger Electron Emitters with b-Particle Emitters", J. of Nuclear Med. 41(12):2089-2097 (2000).
Hansen et al., "Internalization and catabolism of radiolabelled antibodies to the MHC class-II invariant chain by B-cell lymphomas", Biochem. J. 320:293-300, (1996).
Hildebrandt, S. et al, "Expression of CD21, CD22, and the mouse erythrocyte receptor on peripheral B lymphocytes in rheumatoid arthritis", Annals of the Rheumatic Diseases, 47:588-594, 1988.
Inaoki, M. et al., "CD19-Regulated Signaling Thresholds Control Peripheral Tolerance and Autoantibody Production in B Lymphocytes", J Exp. Med., 186(11):1923-1931, 1997.
Inukai et al., "Expression of HLA-DR and its enhancing molecules in muscle fibers in polymyositis", Muscle Nerve 23 (3):385-392 (2000).
Ioachim et al., "Lymphoid Monoclonal Antibodies Reactive with Lung Tumors: Diagnostic Applications", Am. J. Surg. Pathol. 20 (1); 64-71, (1996).
Ishigami et al., "Invariant chain expression in gastric cancer", Cancer Letters 168:87-91, (2001).
Juweid et al., "99Tcm-LL1: a potential new bone marrow imaging agent", Nucl. Med. Commun. 18(2):142-8 (1997).
Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).
Lazova et al., "LN-2 (CD74): A marker to distinguish atypical fibroxanthoma from malignant fibrous histiocytoma", Cancer 79 (11) :2115-2124, (1997).
Li et al., "The Epitope Specificity and Tissue Reactivity of Four Murine Monoclonal Anti-CD22 Antibodies",Cellular Immunology, 118:85-99, 1989.
Maloney, D. G. et al., "IDEC-C2B8 (Rituximab) Anti-CD20 Monoclonal Antibody Therapy in Patients with Relapsed Low-Grade Non-Hodgkins Lymphoma", Blood, 90(6): 2188-2195, 1997.
Maloney et al., "Phase I Clinical Trial using Escalating Single-Dose Infusion of Chimeric Anti-CD20 Monoclonal Antibody (IDEC-C2B8) in Patients with Recurrent B-cell Lymphoma", Blood 84 (8): 2457-2466, (1994).
Marks et al., "By-passing immunization: Human antibodies from V-gene libraries displayed on phage", J. Mol. biol. 222 (3): 581-597, (1991).
Moller et al., "CD74", J. Biol. Regululators of Homeostatic Agents 14: 299-301, (2000).
Ochakovskaya et al., "Therapy of Disseminated B-Cell Lymphoma Xenografts in Severe Combined Immunodeficient Mice with an Anti-CD74 Antibody Conjugated with 111Indium, 67Gallium, or 90Yttrium", Clin Cancer Res; 7:1505-1510, (2001).
Ong et al., "Cell surface expression and metabolism of major histocompatibility complex class II invariant chain (CD74) by diverse cell lines", Immunology 98: 296-302, (1999).
Pastan et al., "Immunotoxins", Cell, 47:641 (1986).
Qu et al., "Internalization and cytotoxic effects of a humanized anti-CD74 antibody, LL1", Proc. annual meeting of Am. Assoc. for Cancer Res., vol. 43: 255 (abstract), Mar. 2002.
Reichmann et al., "Reshaping human antibodies for therapy", Nature, 332:323 (1988).
Roche et al., "Cell Surface HLA-DR-invariant chain complexes are targeted to endosomes by rapid internalization", Proc. Natl. Acad. Sci. USA 90: 8581-8585 (1993).
Rudikoff et al., "Single amino acid substitution altering antigen-binding specificity", Proc. Natl. Acad. Sci. USA 79 (6):1979-83 (1982).

(56) References Cited

OTHER PUBLICATIONS

Salopek et al., "Anti-CD20 chimeric monoclonal antibody (Rituximab) for the treatment of recalcitrant, life-threatening pemphigus vulgaris: Implications for its use in other autoimmune antibody mediated diseases", J. of Investigative Dermatology, 117: 2, p. 542, Abstract No. 916.
Saltzman et al., "Transport rates of proteins in porous materials with known microgeometry", Biophys. J., 55:163 (1989).
Sandhu, "Protein Engineering of Antibodies", Crit. Rev. Biotech., 12:437 (1992).
Schwartz-Albiez et al., "The Carbohydrate Moiety of the CD22 Antigen Can be Modulated by Inhibitors of the Glycosylation Pathway", Leukocyte Typing IV. White Cell Differentiation Antigens, Knapp et al. (eds.), p. 65, Oxford University Press, 1989.
Shan et al., "Apoptosis of malignant human B cells by ligation of CD20 with monoclonal antibodies", Blood 91: 1644-1652, (1998).
Sherwood et al., "Controlled Antibody Delivery Systems", Bio/Technology, 10:1446 (1992).
Singer et al., "Optimal Humanization of 1B4, an Anti-CD18 Murine Monoclonal Antibody, is Achieved by Correct Choice of Human V-Region Framework Sequences", J. Immunol., 150:2844 (1993).
Taylor et al., "Human immunoglobulin transgenes undergo rearrangement, somatic mutation and class switching in mice that lack endogenous IgM", Int. Immun., 6:579 (1994).
Verhoeyen et al., "Reshaping Human Antibodies: Grafting an Antilysozyme Activity", Science, 239:1534 (1988).
Wilson et al., "cDNA Cloning of the B Cell Membrane Protein CD22: A Mediator of B—B Cell Interactions", J. Exp. Med., 173:137 (1991).
Wilson et al., "Genomic Structure and Chromosomal Mapping of the Human CD22 Gene", J. Immunol., 150:5013 (1993).
Wolfe, F., "The epidemiology of drug treatment failure in rheumatoid arthritis", Bailliere's Clinical rheumatology, 9:619-632, 1995.
Wosnick et al., "Rapid construction of large synthetic genes: total chemical synthesis of two different versions of the bovine prochymosin gene", Gene, 60:115 (1987).
Wurflein et al, "Evaluating antibodies for their capacity to induce cell-mediated lysis of malignant B cells", Cancer Res. 58: 3051-3058, (1998). Published online Jul. 1, 1998.
Young et al., "Expression profiling of renal epithelial neoplasms: a method for tumor classification and discovery of diagnostic molecular markers", Am. J. Pathol. 158 (5) : 1639-1651, (2001).
Adang et al., The reconstruction and expression of a Bacillus thuringiensis cryIIIA gene in protoplasts and potato plants:, Plant Molec. Biol., 21:1131 (1993).
Ausubel et al. (eds.), "Gene Synthesis: Assembly of Target Sequences Using Mutually Priming Long Oligonucleotides", Current Protocols in Molecular Biology, pp. 8.2.8-8.2.13 (1990).
Ausubel et al. (eds.), "Gene Synthesis: Assembly of Target Sequences Using Mutually Priming Long Oligonucleotides", Short Protocols in Molec. Biol., 3rd ed., pp. 8.8-8.10, John Wiley & Sons, Inc. (1995).
Baines et al., "Purification of Immunoglobulin G (IgG)", Methods in Molecular Biology, vol. 10, pp. 79-104, Manson (eds.), The Humana Press (1992).
Bambot et al., "Efficient Total Gene Synthesis of 1.35 kb Hybrid α-Lytic Protease Gene using the Polymerase Chain Reaction", PCR Meth. Appl., 2:266 (1993).
Baum et al., "Initial Clinical Results with Technetium-99m-Labeled LL2 Monoclonal Antibody Fragment in the Radioimmunodetection of B-Cell Lymphomas", Cancer 73 (Supp. 3):896 (1994).
Bhat et al., "Human Antilipid A Monoclonal Antibodies Bind to Human B Cells and the i Antigen on Cord Red Blood Cells", J. Immunol., 151(9):5011 (1993).
Carter et al., "Humanization of an anti-P185HER2 antibody for human cancer therapy", Proc. Nat'l Acad. Sci. USA, 89:4285 (1992).
Coligan et al., (eds.), "Production of Monoclonal Antibodies", Current Protocols in Immunology, vol. 1, pp. 2.5.1-2.6.7, 2.7.1-2.7.12, 2.9.1-2.93, 2.10.1-2.10.4, John Wiley & Sons (1991).

Coloma et al., "Design and production of novel tetravalent bispecific antibodies", Nature Biotech., 15:159 (1997).
Dillon et al., "Use of the Polymerase Chain Reaction for the Rapid Construction of Synthetic Genes", Methods in Molecular Biol., vol. 15:PCR Protocols: Curent Methods and Applications, White (ed.), pp. 263-268, Humana Press, Inc. (1993).
Foy et al., "In Vivo-CD40-gp39 Interactions are Essential for Thymus-Dependent Humoral Immunity. II. Prolonged Suppression of the Humoral Immune Response by an Antibody to the Ligand for CD40, gp39", J. Exp. Med., 178:1567 (1993).
Ghetie et al., "Evaluation of Ricin A Chain-Containing Immunotoxins Directed Against CD19 and CD22 Antigens on Normal and Malignant Human B-Cells as Potential Reagents for in Vico Therapy", Cancer Res. May 1, 1988;48 (9):2610-7.
Goldenberg et al., "Targeting, Dosimetry and Radioimmunotherapy of B-cell Lymphomas with Iodine 131-Labeled LL2 Monoclonal Antibody", J. Clin. Oncol., 9:548 (1991).
Goldenberg, "New Developments in Monoclonal Antibodies for Cancer Detection and Therapy", CA—A Cancer Journal for Clinicians, 44:43 (1994).
Green et al., "Antigen-specific human monoclonal antibodies from mice engineered with human Ig heavy and light chain YACs", Nature Genet., 7:13 (1994).
Hekman et al., "Initial Experience with Treatment of Human B Cell Lymphoma with Anti-CD19 Monoclonal Antibody", Cancer Immunology Immunotherapy, 1991, pp. 364-372, vol. 32.
IMURAN patient information leaflet, GlaxoSmithKline 7076598/5093, Oct. 2004.
Jones et al., "Replacing the complementarity-determining regions in a human antibody with those from a mouse", Nature, 321:522 (1986).
Kaminski et al., "Radioimmunotherapy of B-Cell Lymphoma with [131I] Anti-B1 (Anti-CD20) Antibody", The New England Journal of Medicine, 1993, pp. 459-465, vol. 329, No. 7.
Kiener et al., "Stimulation of CD40 with purified soluble gp39 induces proinflammatory responses in human monocytes", J. Immunol., 155(10):4917 (1995) (abstract only).
Kohler et al., "Continuous cultures of fused cells secreting antibody of predefined specificity", Nature, 256:495 (1975).
Kreitman et al., "Pseudomonas exotoxin-based immunotoxins containing the antibody LL2 or LL2-Fab' induce regression of subcutaneous human B-cell lymphoma in mice", Cancer Res. Feb. 15, 1993;53(4):819-25.
Leung et al., "Chimerization of LL2, a Rapidly Internalizing Antibody Specific for B Cell Lymphoma", Hybridoma, 1994, pp. 469-476, vol. 13, No. 6.
Leung et al., "Construction and Characterization of a Humanized, Internalizing B-Cell (CD22)-Specific, Leukemina/Lymphoma Antibody, LL2", Mol. Immunol. 1995, pp. 1413-1427, vol. 32, No. 17/18.
Levine et al., "IgM antibody-related polyneuropathies: B-cell depletion chemotherapy using Rituximab", Neurology, vol. 52, No. 8, pp. 1701-1704, May 12, 1999.
Lonberg et al., "Antigen-specific human antibodies from mice comprising four distinct genetic modifications", Nature, 368:856 (1994).
Longo, D., "Immunotherapy for Non-Hodgkin's Lymphoma", Current Opinion in Oncology, 1996, pp. 353-359, vol. 8, No. 5.
Losman et al., "Baboon Anti-Idiotype Antibodies Mimic a Carcinoembryonic Antigen Epitope", Int. J. Cancer, 46:310 (1990).
Lundberg, B., "Preparation of Drug-Carrier Emulsions Stabilized with Phosphatidylcholine-Surfactant Mixtures", J. Pharm. Sci., 83:72 (1993).
Lundberg et al., "Submicron lipid emulsions containing amphipathic polyethylene glycol for use as drug-carriers with prolonged circulation time", Int. J. Pharm., 134:119 (1996).
Mack et al., "A small bispecific antibody construct expressed as a functional single-chain molecule with high tumor cell cytotoxicity", Proc. Natl. Acad. Sci., 92:7021 (1995).
Mason et al., "Value of monoclonal anti-CD22 (P135) antibodies for the detection of normal and neoplastic B lymphoid cells", Blood, 69:836 (1987) (abstract only).

(56) References Cited

OTHER PUBLICATIONS

Mills et al., "Diagnostic imaging of non-Hodgkin's B-cell lymphoma with anti-lymphomas antibody labeled with Tc-99m", Proc. Am. Assoc. Cancer Res. 34:479 (1993) (Abstract #2857).
Mole et al., "Epitope Mapping", Methods in Molecular Biology, vol. 10:Immunochemical Protocols, Manson (ed.), pp. 105-116, The Humana Press (1992).
Murthy et al., "Lymphoma imaging with a new technetium-99m labelled antibody, LL2", Eur. J. Nucl. Med., 19:394 (1992).
Orlandi et al., "Cloning immunoglobulin variable domains for expression by the polymerase chain reaction", Proc. Nat'l Acad. Sci. USA, 86:3833 (1989).
Pawlak-Byczkowska et al., "Two New Monoclonal Antibodies, EPB-1 and EPB-2, Reactive with Human Lymphoma"; Cancer Research, 1989, pp. 4568-4577, vol. 49, No. 16.
Perrotta et al., "Response to Chronic Relapsing ITP of 10 Years Duration of Retuximab", Blood, vol. 92 (10 Suppl 1, part 1-2), p. 88b, 1998, abstract 3360.
Press et al. "Radiolabeled-Antibody Therapy of B-Cell Lymphoma with Autologous Bone Marrow Support", The New England Journal of Medicine, 1993, pp. 1219-1224, vol. 329, No. 17.
Press et al., "Phase II Trial of 131 I-B1 (anti-CD20) Antibody Therapy with Autologous Stem Cell Transplantation for Relapsed B Cell Lymphomas", The Lancet, 1995, pp. 336-340, vol. 346, No. 8971.
Protheroe et al., "Remission of inflammatory arthropathy in association with anti-CD20 therapy for non-Hodgkin's lymphoma", Rheumatology, vol. 38, No. 11, pp. 1150-1152, Nov. 1999.
Qu et al., "Carbohydrates engineered at antibody constant domains can be used for site-specific conjugation of drugs and chelates", Journal of Immunological Methods, Apr. 15, 1998, pp. 131-144, vol. 213, No. 2.
Rowan et al. "Cross-linking of the CAMPATH-1 antigen (CD52) mediates growth inhibition in human B-and T-lymphoma cell lines, and subsequence emergence of CD52-deficient cells", Immunology, vol. 95, No. 3, pp. 427-436, Nov. 1998.
Shih et al., "Internalization and intracellular Processing of an Anti-B-Cell Lymphoma Monoclonal Antibody, LL2"; Int. J. Cancer, 1994, pp. 538-545, vol. 56.
Stein et al., "Epitope specificity of the anti-(B cell lympoma) monocional antibody, LL2", Cancer Immunology Immunotherapy, vol. 37, No. 5, pp. 293-298, 1993.
The Merck Manual of Diagnosis and Therapy (Seventeenth Edition, Beers et al. eds., Merck Research Laboratoires, Whitehouse Station, NJ, 1999, Chapter 180, "Demyelinating Diseases", pp. 1473-1476.
Theocharis et al., "Charactarization of in Vivo Mutated T Cell Clones from Patients with Systemic Lupus Erythematosus", Clinical immunology and Immunopathology, vol. 74, No. 2, pp. 135-142, Feb. 1995.
Wallace et al., "Efficacy and safety of epratuzumab in patients with moderate/severe flaring systemic lupus erythematosus: results from two randomized, double-blind, placebo-controlled, multicentre studies (Alleviate) and follow-up", Rheumatology (Oxford). Jul. 2013;52(7):1313-22.
Wallace et al., "Efficacy and safety of epratuzumab in patients with moderate/severe active systemic lupus erythematosus: results from Emblem, a phase IIb, randomised, double-blind, placebo-controlled, multicentre study", Ann Rheum Dis. Jan. 2014;73(1):183-90.
Hoelzer, D., "Targeted therapy with monoclonal antibodies in acute lymphoblastic leukemia", Curr Opin Oncol. Nov. 2013;25(6):701-6.
Illidge et al., "Radioimmunotherapy in follicular lymphoma", Best Pract Res Clin Haematol. Jun. 2011;24(2):279-93.
Leonard et al., "Epratuzumab, a humanized anti-CD22 antibody, in aggressive non-Hodgkin's lymphoma: phase I/II clinical trial results", Clin Cancer Res. Aug. 15, 2004;10(16):5327-34.
Leung et al., "An extended primer set for PCR amplification of murine kappa variable regions", Biotechniques. Aug. 1993;15(2):286-92.
Mavromatis et al., "Novel therapies for chronic lymphocytic leukemia", Blood Rev. Jun. 2004;18(2):137-48.
Micallef et al., "Epratuzumab with rituximab, cyclophosphamide, doxorubicin, vincristine, and prednisone chemotherapy in patients with previously untreated diffuse large B-cell lymphoma", Blood. Oct. 13, 2011;118 (15):4053-61.
Nitschke, L., "The role of CD22 and other inhibitory co-receptors in B-cell activation", Curr Opin Immunol. Jun. 2005;17(3):290-7.
Sharkey et al., "Epratuzumab-SN-38: a new antibody-drug conjugate for the therapy of hematologic malignancies", Mol Cancer Ther. Jan. 2012;11(1):224-34.
Steinfeld et al., "Epratuzumab (humanised anti-CD22 antibody) in primary Sjogren's syndrome: an open-label phase I/II study", Arthritis Res Ther. 2006;8(4):R129.
Strand et al., "Epratuzumab for patients with moderate to severe flaring SLE: health-related quality of life outcomes and corticosteroid use in the randomized controlled Alleviate trials and extension study SL0006", Rheumatology (Oxford). Mar. 2014;53(3):502-11.
Wallace et al., "Epratuzumab for systemic lupus erythematosus", Lupus. Apr. 2013;22(4):400-5.

* cited by examiner

FIG. 1A

```
EU_VH     PVQLVQSGAEVKKPGSSVKVSCKASGGTFS RSAII WVRQA
LL2VH     QVQLQESGAELSKPGASVKMSCKASGYTFT SYWLH WIKQR
hLL2VH    QVQLQQSGAEVKKPGSSVKVSCKASGYTFT SYWLH WVRQA
RFB4      EVQLVESGGGLVKPGGSLKLSCAASGFAF  SIYDMS WVRQT
hRFB4     QVQLVQSGAEVKKPGSSVKVSCKASGFTF  SIYDMS WVRQA

EU_VH     PGQGLEWMG GIVPMFGPPNYAQKFQG RVTITADESTNTAY
LL2VH     PGQGLEWIG YIYPRNDYTEYNQNFKD KATLTADKSSSTAY
hLL2VH    PGQGLEWIG YIYPRNDYTEYNQNFKD KATITADESTNTAY
RFB4      PEKRLEW VA YISSGGGTTYYPDTVKG RF TISRDNAKNTLY
hRFB4     PGQGLEW VA YISSGGGTTYYPDTVKG RF TITADESTNTAY

EU_VH     MELSSLRSEDTAFYFCAG GYGIYSPE
LL2VH     MQLSSLTSEDSAVYYCAR RDITT-FY
hLL2VH    MELSSLRSEDTAFYFCAR RDITT-FY
RFB4      LQMSSLKSEDTAMYYCAR HSGYGSSYGVLFAY
hRFB4     MELSSLRSEDTAFYFCAR HSGYGSSYGVLFAY

NEWM_VH   WGQGSLVTVSS
LL2VH     WGQGTTLTVSS
hLL2VH    WGQGTTVTVSS
RFB4      WGQGTLVTVSA
hRFB4     WGQGTLVTVSS
```

FIG. 1B

```
              1        10        20      27ABCDEF  30
REIVk    DIQMTQSPSSLSASVGDRVTITC|QASQ------DIIKYLN|
LL2Vk    DIQLTQSPSSLAVSAGENVTMSC|KSSQSVLYSANHKNYLA|
hLL2Vk   DIQLTQSPSSLSASVGDRVTMSC|KSSQSVLYSANHKNYLA|
RFB4     DIQLTQTTSSLSASLGDRVT ISC|RASQDISNYLN      |
hRFB4    DIQLTQSPSSLSASVGDRVT ISC|RASQDISNYLN      |

40        50        60        70
REIVk    WYQQTPGKAPKLLIY|EASNLQA|GVPSRFSGSGSGTDYTFT
LL2Vk    WFQQKPGQSPKLLIY|WASTRES|GVPDRFTGSGSGTDFTLT
hLL2Vk   WYQQKPGKAPKLLIY|WASTRES|GVPSRFSGSGSGTDFTFT
RFB4     WYQQKPDGTVKLLIY|YTSILHS|GVPSRFSGSGSGTDYSLT
hRFB4    WYQQKPGKAPKLLIY|YTSILHS|GVPSRFSGSGSGTDYTFT 80        90       100
REIVk    ISSLQPEDIATYYC|QQYQSLPYT|FGQGTKLQITR
LL2Vk    ISRVQVEDLAIYYC|HQYLSS-WT|FGGGTKLEIKR
hLL2Vk   ISSLQPEDIATYYC|HQYLSS-WT|FGGGTKVQIKR
RFB4     ISNLEQEDFATYFC|QQGNTLPWT|FGGGTKLEIK
hRFB4    ISSLQPEDIATYYC|QQGNTLPWT|FGGGTKVQIKR
```

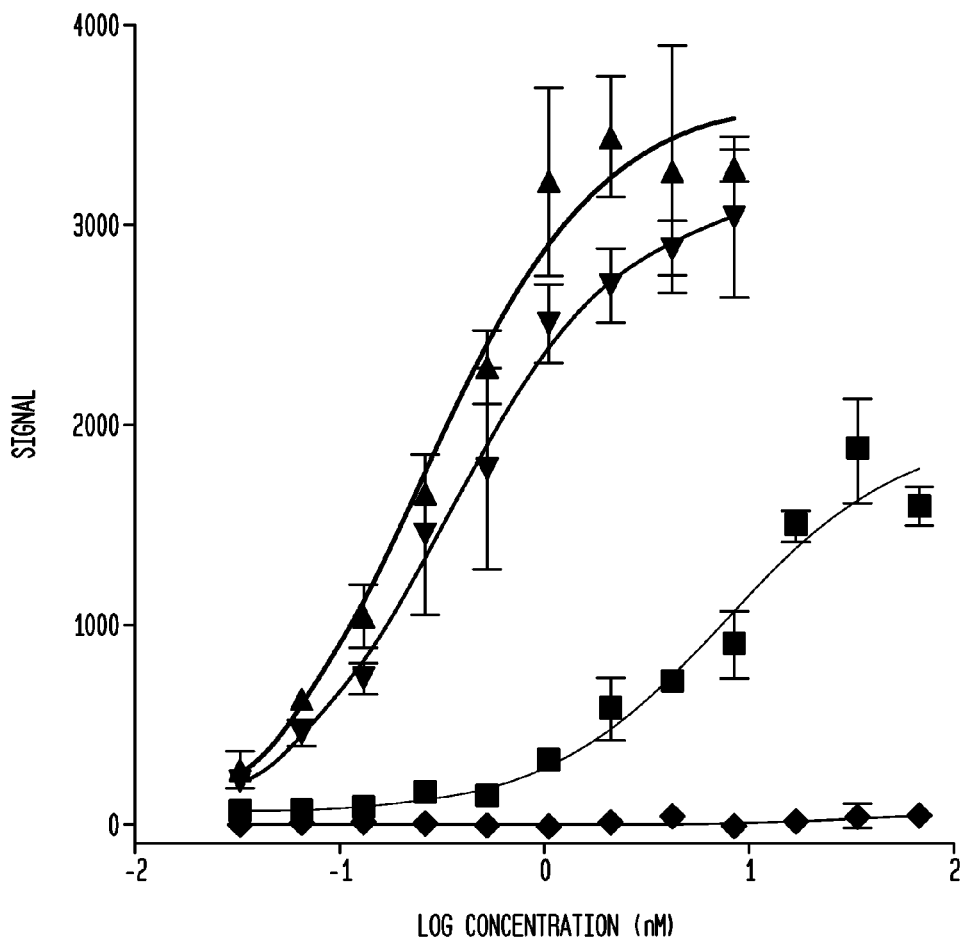

*FIG. 5*

| % UNTREATED | | | |
|---|---|---|---|
|  | Emab | hRFB4 | P VALUE |
| CD22 | 8.3 | 6.6 | 0.0005 |
| CD19 | 49.3 | 41.2 | 0.0019 |
| CD21 | 51.4 | 44.5 | 0.0164 |
| CD79b | 74.7 | 59.2 | 0.0087 |
| DEPLETION | 99.3 | 87.3 | 0.0045 |

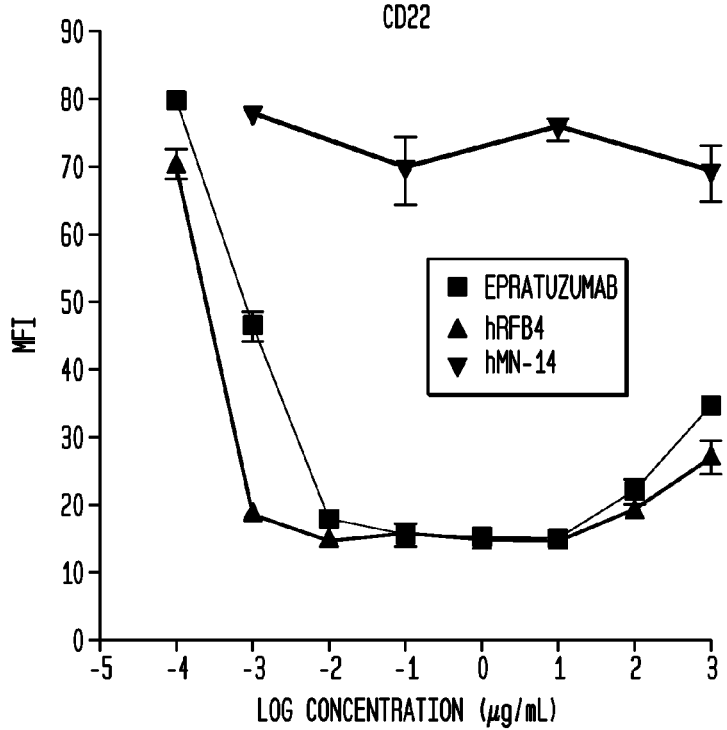
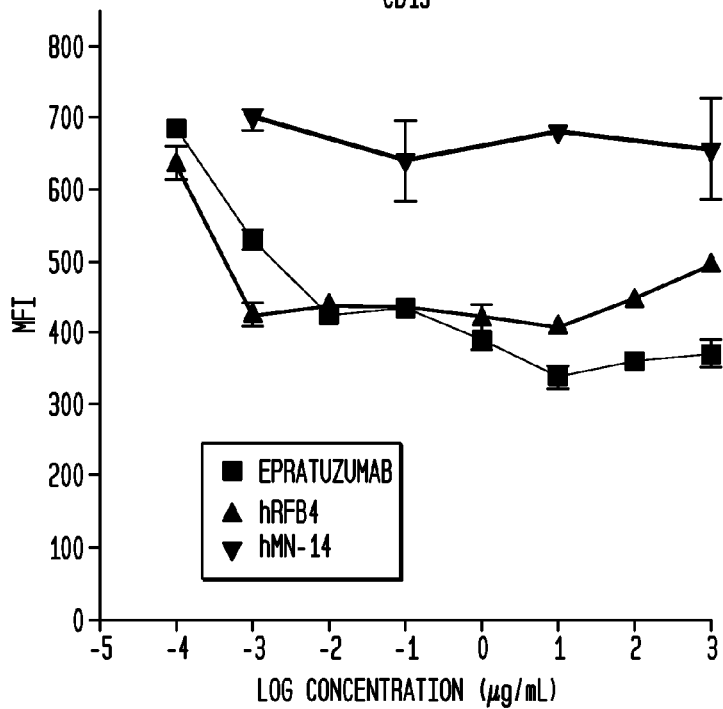

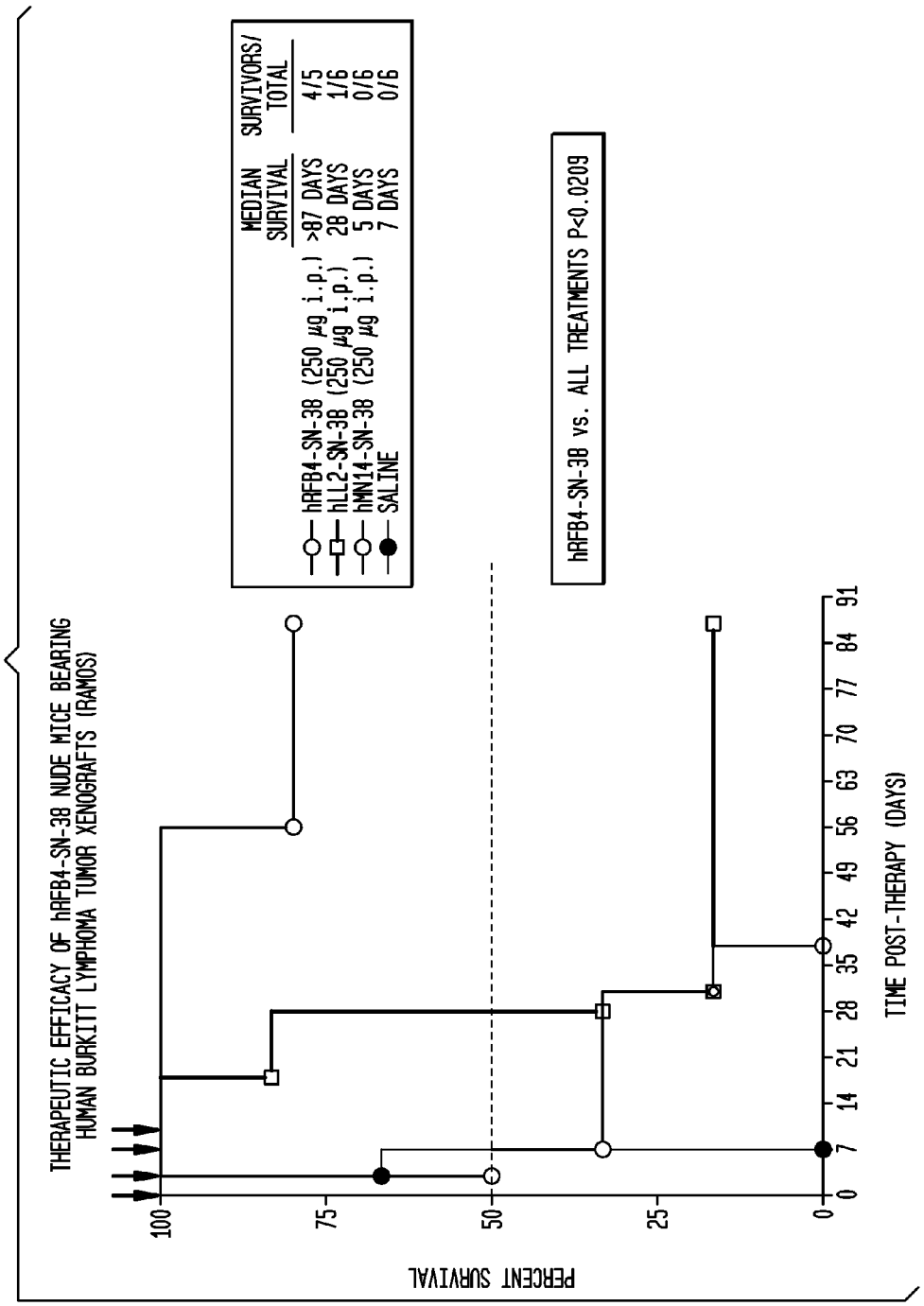

HUMANIZED ANTI-CD22 ANTIBODY

RELATED APPLICATIONS

This application is a continuation of U.S. patent application Ser. No. 14/603,011, filed Jan. 22, 2015, which claims the benefit under 35 U.S.C. 119(e) of Provisional U.S. Patent Application Ser. No. 61/944,295, filed Feb. 25, 2014, the priority application incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jan. 8, 2015, is named IMM345US1_.txt and is 67,443 bytes in size.

FIELD OF THE INVENTION

The present invention concerns compositions and methods of use of humanized RFB4 (hRFB4) anti-CD22 antibodies. Preferably, hRFB4 comprises the heavy chain complementarity determining region (CDR) sequences CDR1 (IYDMS, SEQ ID NO:1), CDR2 (YISSGGGT-TYYPDTVKG, SEQ ID NO:2) and CDR3 (HS-GYGSSYGVLFAY, SEQ ID NO:3) and the light chain CDR sequences CDR1 (RASQDISNYLN, SEQ ID NO:4), CDR2 (YTSILHS, SEQ ID NO:5) and CDR3 (QQGNTLPWT, SEQ ID NO:6), along with heavy chain framework region (FR) amino acid residues Q1, V5, F27, S30, V48, A49, R67, F68, R98, T117 and L118, and light chain residues L4, I21, S22, K39, Y71, G100, V104, and K107. More preferably, the hRFB4 antibody comprises the heavy chain framework region (FR) amino acid residues Q6, A9, E10, V11, K12, K13, S16, V18, K19, V20, K23, T28, Q43, T71, A72, E74, S75, T76, T78, A79, M81, E82, L83, S84, S88, F93, and F95, and light chain residues D70, F73, I83, Y87, and Q105. Most preferably, the heavy and light chain variable region sequences of hRFB4 comprise SEQ ID NO:7 and SEQ ID NO:8, respectively. In various embodiments, hRFB4 anti-CD22 antibody induces trogocytosis of multiple surface markers, which include, but are not limited to, CD19, CD20, CD21, CD22 and/or CD79b on normal, lupus, and malignant B cells (donor cells) via leukocytes, including monocytes, NK cells and granulocytes (recipient cells). Trogocytosis-inducing anti-CD22 antibodies are of use in therapy of various disease states, including but not limited to autoimmune diseases, immune dysfunction diseases and hematopoietic cancers. The hRFB4 antibody may be used alone, or in combination with other agents, which include one or more different antibodies. Where a combination of two antibodies is desirable, a bispecific antibody derived from the two antibodies of interest may be used in lieu of a combination of such antibodies. Bispecific antibodies are preferred to administration of combinations of separate antibodies, due to cost and convenience. However, where combinations of separate antibodies provide improved safety or efficacy, the combination may be utilized. One preferred form of the bispecific antibody is a hexavalent antibody (HexAb) that is made as a DOCK-AND-LOCK™ complex.

BACKGROUND

[04] CD22 is a 135-kD type I transmembrane sialoglycoprotein of the immunoglobulin (Ig) superfamily. CD22 expression is specific to B cells and is developmentally regulated so that expression is limited in pro-B and pre-B cells (Dorner & Goldenberg, 2007, Ther Clin Risk Manag 3:954-59). As B cells mature, expression increases and localization of CD22 shifts to the cell surface (Dorner & Goldenberg, 2007). CD22 is strongly expressed on follicular, mantle and marginal-zone B cells, but is weakly present in germinal B cells (Dorner & Goldenberg, 2007). CD22 is an inhibitory co-receptor that downmodulates B-cell receptor (BCR) signaling by setting a signaling threshold that prevents overstimulation of B cells (Nitschke, 2005, Curr Opin Immunol 17:290-97).

Antibodies against CD22, such as epratuzumab (hLL2), have been used for treatment of a variety of cancers and autoimmune diseases, including but not limited to acute lymphoblastic leukemia (Hoelzer et al., 2013, Curr Opin Oncol 25:701-6), chronic lymphocytic leukemia (Macromatis & Cheson, 2004, Blood Rev 18:137-48), non-Hodgkin's lymphoma (Leonard et al., 2004, Clin Cancer Res 10:5327-34; Dorner & Goldenberg, 2007), follicular lymphoma (Illidge & Morchhauser, 2011, Best Pract Res Clin Haematol 24:279-93), diffuse large B-cell lymphoma (Micallef et al., 2011, Blood 118:4053-61), mantle cell lymphoma (Sharkey et al., 2012, Mol Cancer Ther 11:224-34), systemic lupus erythematosus (Dorner & Goldenberg, 2007; Strand et al., 2013, Rheumatology Nov. 22, 2013 Epub ahead of print; Wallace & Goldenberg, 2013, Lupus 22:400-5; Wallace et al., 2013, Rheumatology 52:1313-22; Wallace et al., 2014, Ann Rheum Dis 73:183-90), and primary Sjögren's syndrome (Steinfeld et al., 2006, Arthritis Res Ther 8:R129; Dorner & Goldenberg, 2007). A phase III clinical trial of epratuzumab in systemic lupus erythematosus is currently in progress (see, e.g., ClinicalTrials.gov, "Study of Epratuzumab versus Placebo in Subjects with Moderate to Severe General Systemic Lupus Erythematosus (EMBODY 1)"). Because CD22 regulates B-cell functions and survival, it is an important link for modulating humoral immunity and proliferation of B-cell lymphomas and a target for therapeutic antibodies in cancer and autoimmune disease (Dorner & Goldenberg, 2007).

RFB4 is a murine anti-CD22 antibody that was initially thought to bind to the same epitope group (epitope B) of CD22 as epratuzumab (Stein et al., 1993, Cancer Immunol Immunother 37:293-8). However, more recent studies provided evidence that RFB4 and epratuzumab respectively bind to domain 3 and domain 2 of CD22. A need exists for a humanized form of RFB4, with reduced immunogenicity in humans that shows enhanced B cell binding and efficacy against B cell related diseases, compared with epratuzumab.

SUMMARY

The present invention concerns compositions and methods of use of humanized RFB4 (hRFB4) anti-CD22 antibodies or antigen-binding fragments thereof. Preferably, the hRFB4 antibody or fragment thereof comprises the heavy chain complementarity determining region (CDR) sequences CDR1 (IYDMS, SEQ ID NO:1), CDR2 (YISSGGGTTYYPDTVKG, SEQ ID NO:2) and CDR3 (HSGYGSSYGVLFAY, SEQ ID NO:3) and the light chain CDR sequences CDR1 (RASQDISNYLN, SEQ ID NO:4), CDR2 (YTSILHS, SEQ ID NO:5) and CDR3 (QQGNTLPWT, SEQ ID NO:6), along with heavy chain framework region (FR) amino acid residues Q1, V5, F27, S30, V48, A49, R67, F68, R98, T117 and L118, and light chain residues L4, I21, S22, K39, Y71, G100, V104, and K107. More preferably, the hRFB4 antibody comprises the heavy chain framework region (FR) amino acid residues Q6, A9, E10, V11, K12, K13, S16, V18, K19, V20, K23, T28, Q43, T71, A72, E74, S75, T76, T78, A79, M81, E82, L83, S84, S88, F93, and F95, and light chain residues D70, F73, I83, Y87, and Q105. Most preferably, the heavy and light chain variable region sequences of hRFB4 comprise SEQ ID NO:7 and SEQ ID NO:8, respectively.

In other preferred embodiments, the hRFB4 antibody or fragment thereof induces trogocytosis of multiple surface markers, which include, but are not limited to, CD19, CD21, CD20, CD22 and CD79b on normal, lupus, and malignant B cells via monocytes, NK cells and granulocytes. Most preferably, the hRFB4 antibody or fragment thereof displays little or negligible direct cytotoxicity to normal B cells based on an in vitro cell proliferation assay that shows less than 20% growth inhibition when compared with untreated control, yet reduces CD19, CD21, CD20, CD22, and CD79b by 80% or more of the untreated control via trogocytosis in the presence of peripheral blood mononuclear cells (PBMCs) or purified FcγR-positive cells, such as NK cells, monocytes and granulocytes. The ability of the hRFB4 antibody or fragment thereof to induce trogocytosis without incurring direct cytotoxicity to B cells thus provides an unexpected and substantial advantage in treating autoimmune diseases, such as systemic lupus erythematosus (SLE), ANCA-associated vasculitides, and other autoimmune diseases.

In certain embodiments, administration of a hRFB4 antibody or fragment thereof induces trogocytosis in B cells, resulting in decreased levels of CD19, CD20, CD21, CD22 and CD79b on the surface of affected B cells. The reduction in these regulators of antigen-specific B-cell receptor (BCR), particularly CD19, inhibits B cell activation in response to T cell-dependent antigens and has a therapeutic effect on autoimmune and immune dysfunction diseases, which are mediated at least in part by B cell activation.

Exemplary autoimmune or immune dysfunction diseases that may potentially be treated with hRFB4 antibody or fragments thereof include acute immune thrombocytopenia, chronic immune thrombocytopenia, dermatomyositis, Sydenham's chorea, myasthenia gravis, systemic lupus erythematosus, lupus nephritis, rheumatic fever, polyglandular syndromes, bullous pemphigoid, pemphigus vulgaris, diabetes mellitus (e.g., juvenile diabetes), Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, fibrosing alveolitis, graft-versus-host disease (GVHD), organ transplant rejection, sepsis, septicemia and inflammation.

Hematopoietic malignancies, such as non-Hodgkin's lymphoma, B-cell acute and chronic lymphoid leukemias, Burkitt lymphoma, Hodgkin's lymphoma, hairy cell leukemia, multiple myeloma and Waldenstrom's macroglobulinemia may also be treated with hRFB4 antibody or fragments thereof. The hRFB4 antibody may be used alone or in combination with one or more other antibodies against B-cell leukemias or lymphomas. Antibodies against B-cell surface proteins, such as CD19, CD20, CD21, CD22 and/or CD79b, are known in the art and any such known antibody might be used in the claimed compositions and methods. An exemplary anti-CD20 antibody is hA20 (veltuzumab), disclosed for example in U.S. Pat. No. 7,251,164, the Examples section of which is incorporated herein by reference. Other known anti-CD20 antibodies of potential use include, but are not limited to, rituximab (Genentech, South San Francisco, Calif.), GA101 (obinutuzumab; RO5072759, Roche, Basle, Switzerland), ofatumumab (GlaxoSmithKline, London, England), ocrelizumab (Roche, Nutley, N.J.), AME-133v (ocaratuzumab, MENTRIK Biotech, Dallas, Tex.), ibritumomab (Spectrum Pharmaceuticals, Irvine, Calif.) and PRO131921 (Genentech, South San Francisco, Calif.). An exemplary anti-CD19 antibody is hA19, disclosed for example in U.S. Pat. No. 7,109,304, the Examples section of which is incorporated herein by reference. Other known anti-CD19 antibodies of potential use include, but are not limited to, XmAb5574 (Xencor, Monrovia, Calif.), 5F3 (OriGene, Rockville, Md.), 4G7 (Pierce, Rockford, Ill.), 2E2 (Pierce, Rockford, Ill.), 1G9 (Pierce, Rockford, Ill.), LT19 (Santa Cruz Biotechnology, Santa Cruz, Calif.) and HD37 (Santa Cruz Biotechnology, Santa Cruz, Calif.). An exemplary anti-CD22 antibody is hLL2 (epratuzumab), disclosed for example in U.S. Pat. No. 7,074,403, the Examples section of which is incorporated herein by reference. Other known anti-CD22 antibodies of potential use include, but are not limited to, inotuzumab (Pfizer, Groton, Conn.), CAT-3888 (Cambridge Antibody Technology Group, Cambridge, England), CAT-8015 (Cambridge Antibody Technology Group, Cambridge, England), and HB22.7 (Duke University, Durham, N.C.). Exemplary anti-CD21 antibodies of potential use include, but are not limited to, LS-B7297 (LSBio, Seattle, Wash.), HB5 (eBioscience, San Diego, Calif.), A-3 (Santa Cruz Biotechnology, Santa Cruz, Calif.), D-19 (Santa Cruz Biotechnology, Santa Cruz, Calif.), Bly4 (Santa Cruz Biotechnology, Santa Cruz, Calif.), 1F8 (Abcam, Cambridge, Mass.) and Bu32 (BioLegend, San Diego, Calif.). Exemplary anti-CD79b antibodies of potential use include, but are not limited to, B29 (LSBio, Seattle, Wash.), 3A2-2E7 (LSBio, Seattle, Seattle, Wash.), CD3-1 (eBioscience, San Diego, Calif.) and SN8 (Santa Cruz Biotechnology, Santa Cruz, Calif.). Many such antibodies are publicly known and/or commercially available and any such known antibody may be utilized. In various embodiment, the antibody may be bispecific or multispecific. The antibody may include human constant regions of IgG1, IgG2, IgG3, or IgG4.

In certain embodiments, a hRFB4 antibody or fragment thereof may be administered to a patient as part of a combination of antibodies. The antibodies may bind to different epitopes of the same antigen or to different antigens. Preferably, the antigens are selected from the group consisting of BCL-1, BCL-2, BCL-6, CD1a, CD2, CD3, CD4, CD5, CD7, CD8, CD10, CD11b, CD11c, CD13, CD14, CD15, CD16, CD19, CD20, CD21, CD22, CD23, CD25, CD33, CD34, CD38, CD40, CD40L, CD41a, CD43, CD45, CD47, CD55, CD56, CCD57, CD59, CD64, CD71, CD79a, CD79b, CD117, CD138, CXCR4, FMC-7 and HLA-DR. However, antibodies against other antigens of use for therapy of cancer, autoimmune diseases or immune dysfunction diseases are known in the art, as discussed below, and antibodies against any such disease-associated antigen known in the art may be utilized. In a particularly preferred embodiment, the combination may involve use of two or more antibodies that bind to different epitopes of CD22, such as an hRFB4 antibody and an hLL2 antibody. The combination of antibodies may be used as intact IgG antibodies, antibody fragments, or immunoconjugates attached to one or more other therapeutic agents.

In more preferred embodiments, the allotype of the antibody may be selected to minimize host immunogenic response to the administered antibody, as discussed in more detail below. A preferred allotype is a non-G1m1 allotype (nG1m1), such as G1m3, G1m3,1, G1m3,2 or G1m3,1,2. The non-G1m1 allotype is preferred for decreased antibody immunoreactivity. Surprisingly, repeated subcutaneous administration of concentrated nG1m1 antibody was not found to induce significant immune response, despite the enhanced immunogenicity of subcutaneous administration.

BRIEF DESCRIPTION OF THE DRAWINGS

The following drawings are provided to illustrate preferred embodiments of the invention. However, the claimed subject matter is in no way limited by the illustrative embodiments disclosed in the drawings.

FIG. 1A. Design of hRFB4 VH. Comparison of the heavy chain variable region sequences (VH) from the EU human antibody (FR1-FR3) (SEQ ID NO:9), the murine anti-CD22 LL2 antibody (SEQ ID NO:10), the humanized anti-CD22 LL2 antibody (SEQ ID NO:11), the murine anti-CD22 RFB4 antibody (SEQ ID NO:12), FR4 of the human NEWM antibody (SEQ ID NO:13) and the humanized RFB4 antibody (SEQ ID NO:7). The CDRs (shown in boxes) of RFB4 were grafted onto the frameworks of hLL2. Eight residues in the VH frameworks of hRFB4 are retained from RFB4, thus differing from the corresponding residues in hLL2. Underlined residues are those differing from the human EU or NEWM VH sequences.

FIG. 1B. Design of hRFB4 Vk. Comparison of the light chain variable region sequences (Vk) from the REI human antibody (SEQ ID NO:14), the murine anti-CD22 LL2 antibody (SEQ ID NO:15), the humanized anti-CD22 LL2 antibody (SEQ ID NO:16), the murine anti-CD22 RFB4 antibody (SEQ ID NO:17), and the humanized RFB4 antibody (SEQ ID NO:8). The CDRs (shown in boxes) of RFB4 were grafted onto the frameworks of hLL2. Two residues in the Vk frameworks of hRFB4 are retained from RFB4, thus differing from the corresponding residues in hLL2. Underlined residues are those differing from the human REI VK sequence.

FIG. 2. Comparative binding affinity for CD22+ Daudi cells of hLL2 IgG, hRFB4 IgG, chimeric RFB4 conjugated to AD2 peptide, and hMN-14 IgG, as determined by ELISA. The binding affinity of hRFB4 as determined for Daudi cells is about 10-fold higher than that of hLL2 and about 30% higher than the chimeric RFB4.

FIG. 5. Tabular summary of the data from FIG. 3, showing levels of CD22, CD19, CD21 and CD79b and B cells relative to control.

FIG. 6A. Consistent with its 10-fold higher binding affinity for CD22 in Daudi cells, hRFB4 is more effective than hLL2 in inducing trogocytosis of CD22 from Daudi cell. These results show that the minimal concentration of hRFB4 to induce the maximal level of trogocytosis is 1 ng/mL, as compared to 10 ng/mL of hLL2.

FIG. 6B. Consistent with its 10-fold higher binding affinity for CD22 in Daudi cells, hRFB4 is more effective than hLL2 in inducing trogocytosis of CD19 from Daudi cell. These results show that the minimal concentration of hRFB4 to induce the maximal level of trogocytosis is 1 ng/mL, as compared to 10 ng/mL of hLL2.

FIG. 7. In vivo efficacy of hRFB4-SN-38 immunoconjugate in nude mice with Ramos lymphoma xenografts, compared with hLL2-SN-38 immunoconjugate.

DETAILED DESCRIPTION

Definitions

Figure 3:
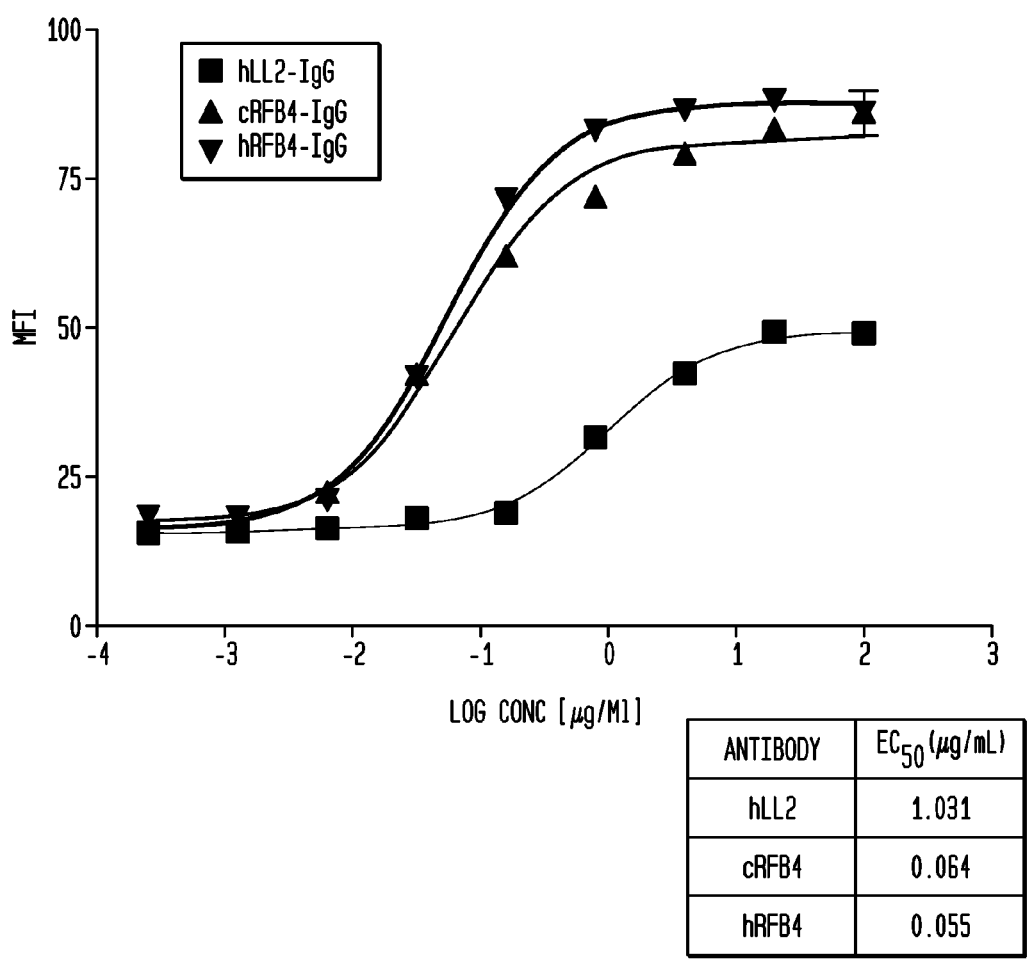
FIG. 3. Comparative binding affinity for CD22+ Daudi cells of hLL2 IgG, cRFB4 IgG, and hRFB4 IgG, as determined by flow cytometry. Binding activity at indicated concentrations is given as the MFI. Measurements were performed in triplicate; standard deviations are shown as bars. Based on the EC50, the affinity of hRFB4 for Daudi was 0.4 nM, equivalent to cRFB4, and 19-fold higher than hLL2 (6.9 nM).

The following definitions are provided to facilitate understanding of the disclosure herein. Where a term is not specifically defined, it is used in accordance with its plain and ordinary meaning.

As used herein, the terms "a", "an" and "the" may refer to either the singular or plural, unless the context otherwise makes clear that only the singular is meant.

An "antibody" refers to a full-length (i.e., naturally occurring or formed by normal immunoglobulin gene fragment recombinatorial processes) immunoglobulin molecule (e.g., an IgG antibody).

An "antibody fragment" is a portion of an antibody such as F(ab')$_2$, F(ab)$_2$, Fab', Fab, Fv, scFv, single domain antibodies (DABs or VHHs) and the like, including half-molecules of IgG4 (van der Neut Kolfschoten et al., 2007, Science 317:1554-1557). Regardless of structure, an antibody fragment binds with the same antigen that is recognized by the intact antibody. For example, an anti-CD22 antibody fragment binds with an epitope of CD22. The term "antibody fragment" also includes isolated fragments consisting of the variable regions, such as the "Fv" fragments consisting of the variable regions of the heavy and light chains, recombinant single chain polypeptide molecules in which light and heavy chain variable regions are connected by a peptide linker ("scFv proteins"), and minimal recognition units consisting of the amino acid residues that mimic the hypervariable region.

A "chimeric antibody" is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species; e.g., a rodent antibody, are transferred from the heavy and light variable chains of the rodent antibody into human heavy and light variable domains, including human framework region (FR) sequences. The constant domains of the antibody molecule are derived from those of a human antibody.

A "human antibody" is an antibody obtained from transgenic mice that have been genetically engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. (See, e.g., McCafferty et al., Nature 348:552-553 (1990) for the production of human antibodies and fragments thereof in vitro, from immunoglobulin variable domain gene repertoires from unimmunized donors). In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g. Johnson and Chiswell, Current Opinion in Structural Biology 3:5564-571 (1993). Human antibodies may also be generated by in vitro activated B cells. (See, U.S. Pat. Nos. 5,567,610 and 5,229,275).

A "therapeutic agent" is an atom, molecule, or compound that is useful in the treatment of a disease. Examples of therapeutic agents include but are not limited to antibodies, antibody fragments, drugs, cytokine or chemokine inhibitors, pro-apoptotic agents, tyrosine kinase inhibitors, toxins, enzymes, nucleases, hormones, immunomodulators, antisense oligonucleotides, siRNA, RNAi, chelators, boron compounds, photoactive agents, dyes and radioisotopes.

A "diagnostic agent" is an atom, molecule, or compound that is useful in diagnosing a disease. Useful diagnostic agents include, but are not limited to, radioisotopes, dyes, contrast agents, fluorescent compounds or molecules and enhancing agents (e.g., paramagnetic ions). Preferably, the diagnostic agents are selected from the group consisting of radioisotopes, enhancing agents, and fluorescent compounds.

An "immunoconjugate" is a conjugate of an antibody with an atom, molecule, or a higher-ordered structure (e.g., with a liposome), a therapeutic agent, or a diagnostic agent.

A "naked antibody" is generally an entire antibody that is not conjugated to a therapeutic agent. This is so because the Fc portion of the antibody molecule provides effector functions, such as complement fixation and ADCC (antibody dependent cell cytotoxicity) that set mechanisms into action that may result in cell lysis. However, it is possible that the Fc portion is not required for therapeutic function, with other mechanisms, such as apoptosis, coming into play. Naked antibodies include both polyclonal and monoclonal antibodies, as well as certain recombinant antibodies, such as chimeric, humanized or human antibodies.

As used herein, the term "antibody fusion protein" is a recombinantly produced antigen-binding molecule in which an antibody or antibody fragment is linked to another protein or peptide, such as the same or different antibody or antibody fragment or a DDD or AD peptide (of the DOCK-AND-LOCK™ complexes described below). The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase.

A "multispecific antibody" is an antibody that can bind simultaneously to at least two targets that are of different structure, e.g., two different antigens, two different epitopes on the same antigen, or a hapten and/or an antigen or epitope. A "multivalent antibody" is an antibody that can bind simultaneously to at least two targets that are of the same or different structure. Valency indicates how many binding arms or sites the antibody has to a single antigen or epitope; i.e., monovalent, bivalent, trivalent or multivalent. The multivalency of the antibody means that it can take advantage of multiple interactions in binding to an antigen, thus increasing the avidity of binding to the antigen. Specificity indicates how many antigens or epitopes an antibody is able to bind; i.e., monospecific, bispecific, trispecific, multispecific. Using these definitions, a natural antibody, e.g., an IgG, is bivalent because it has two binding arms but is monospecific because it binds to one epitope. Multispecific, multivalent antibodies are constructs that have more than one binding site of different specificity.

A "bispecific antibody" is an antibody that can bind simultaneously to two targets which are of different structure. Bispecific antibodies (bsAb) and bispecific antibody fragments (bsFab) may have at least one arm that specifically binds to, for example, a B cell, T cell, myeloid-, plasma-, and mast-cell antigen or epitope and at least one other arm that specifically binds to a targetable conjugate that bears a therapeutic or diagnostic agent. A variety of bispecific antibodies can be produced using molecular engineering. Included herein are bispecific antibodies that target a cancer-associated antigen and also an immunotherapeutic T cell, such as CD3-T cells.

The term "direct cytotoxicity" refers to the ability of an agent to inhibit the proliferation or induce the apoptosis of a cell grown in an optimized culture medium in which only the agent and the cell are present.

Trogocytosis

Trogocytosis (also referred to as shaving in the literature) is a process by which transfer of membrane-bound proteins and membrane components occur between two different types of live cells associated to form an immunological synapse. As a result, the membrane-bound proteins and membrane components are transferred from the donor cells to the recipient cells. Both unidirectional and bidirectional trogocytosis between the two interacting cells may occur. One prominent example of trogocytosis is the extraction of surface antigens from antigen-presenting cells (APCs) by T cells (Joly & Hudrisier, 2003, Nat Immunol 4:85). The process involves transfer of plasma membrane fragments from the APC to the lymphocyte (Joly & Hudrisier, 2003). Intercellular transfer of T cell surface molecules to APCs has also been reported (Nolte-'t Hoen et al, 2004, Eur J Immunol 34: 3115-25; Busch et al 2008, J Immunol 181: 3965-73) via mechanisms that may include trogocytosis, exosome formation and ectodomain shedding (Busch et al 2008, ibid).

Trogocytosis can also occur between natural killer (NK) cells and tumors and can convert activated NK cells into suppressor cells, via uptake of the immunosuppressive HLA-G molecule, which protects the tumor cells from cytolysis (Caumartin et al., 2007, EMBO J 26:423-30). CD4+ and CD8+ T cells can, respectively, acquire MHC Class II and MHC Class I molecules from APCs in an antigen-specific manner (Caumartin et al., 2007). Trogocytosis of HLA-DR, CD80 and HLA-G1 from APCs to T cells has been shown to occur in humans (Caumartin et al., 2007). After acquiring HLA-DR and CD80, T cells stimulated resting T cells in an antigen-specific manner, acting as APCs themselves (Caumartin et al., 2007). More generally, trogocytosis may act to regulate immune system responsiveness to disease-associated antigens and can either stimulate or suppress immune response (Ahmed et al., 2008, Cell Mol Immunol 5:261-69).

The effects of trogocytosis on therapeutic antibody responsiveness and the induction of trogocytosis by therapeutic antibodies remain poorly understood. It has been suggested that induction of trogocytosis by excess amounts of rituximab may result in removal of rituximab-CD20 complexes from tumor cell surfaces by monocytes, producing antigenic modulation (shaving) and rituximab-resistant tumor cells (Beum et al., 2006, J Immunol 176:2600-8). Thus, use of lower, more frequent doses of rituximab to reduce antigen shaving has been suggested (Beum et al., 2006). Transfer of rituximab/CD20 complexes to monocytes is mediated by FcγR and it has also been suggested that polymorphisms in FcγRII and FcγRIII may affect the degree of antibody-induced shaving and predict responsiveness to antibody therapy (Beum et al., 2006). In this regard, use of antibodies or other inhibitors that block trogocytosis may enhance efficacy and reduce tumor cell escape from cytotoxicity (Beum et al., 2006). On the other hand, the functional consequences of antibody-mediated trogocytosis to confer therapeutic benefits are less explored.

Monoclonal Antibodies

The compositions, formulations and methods described herein may include monoclonal antibodies. Rodent monoclonal antibodies to specific antigens may be obtained by methods known to those skilled in the art. (See, e.g., Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991)). General techniques for cloning murine immunoglobulin variable domains have been disclosed, for example, by the publication of Orlandi et al., Proc. Nat'l Acad. Sci. USA 86: 3833 (1989).

Chimeric Antibodies

A chimeric antibody is a recombinant protein that contains the variable domains including the CDRs derived from one species of animal, such as a rodent antibody, while the remainder of the antibody molecule; i.e., the constant domains, is derived from a human antibody. Techniques for constructing chimeric antibodies are well known to those of skill in the art. As an example, Leung et al., Hybridoma 13:469 (1994), disclose how they produced an LL2 chimera by combining DNA sequences encoding the $V_k$ and $V_H$ domains of LL2 monoclonal antibody, an anti-CD22 antibody, with respective human and $IgG_1$ constant region domains. This publication also provides the nucleotide sequences of the LL2 light and heavy chain variable regions, $V_k$ and $V_H$, respectively.

Humanized Antibodies

A chimeric monoclonal antibody can be humanized by replacing the sequences of the murine FR in the variable domains of the chimeric antibody with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. (See, e.g., Tempest et al., Biotechnology 9:266 (1991) and Verhoeyen et al., Science 239: 1534 (1988)). Techniques for producing humanized antibodies are disclosed, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993).

Human Antibodies

A fully human antibody can be obtained from a transgenic non-human animal. (See, e.g., Mendez et al., Nature Genetics, 15: 146-156, 1997; U.S. Pat. No. 5,633,425.) Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Pharmacol.*

3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XENOMOUSE® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XENOMOUSE® immunized with a target antigen will produce human antibodies by the normal immune response, which may be harvested and/or produced by standard techniques discussed above. A variety of strains of XENOMOUSE® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Antibody Cloning and Production

Various techniques, such as production of chimeric or humanized antibodies, may involve procedures of antibody cloning and construction. The antigen-binding $V_\kappa$ (variable light chain) and $V_H$ (variable heavy chain) sequences for an antibody of interest may be obtained by a variety of molecular cloning procedures, such as RT-PCR, 5'-RACE, and cDNA library screening. The V genes of an antibody from a cell that expresses a murine antibody can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci., USA*, 86: 3833 (1989)). Based on the V gene sequences, a humanized antibody can then be designed and constructed as described by Leung et al. (*Mol. Immunol.*, 32: 1413 (1995)).

cDNA can be prepared from any known hybridoma line or transfected cell line producing a murine antibody by general molecular cloning techniques (Sambrook et al., Molecular Cloning, A laboratory manual, $2^{nd}$ Ed (1989)). The $V_\kappa$ sequence for the antibody may be amplified using the primers VK1BACK and VK1FOR (Orlandi et al., 1989) or the extended primer set described by Leung et al. (BioTechniques, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for $V_\kappa$ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the $V_\kappa$ and $V_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human antibody. Alternatively, the $V_\kappa$ and $V_H$ expression cassettes can be excised and subcloned into a single expression vector, such as pdHL2, as described by Gillies et al. (*J. Immunol. Methods* 125:191 (1989) and also shown in Losman et al., *Cancer,* 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:19) and veltuzumab (SEQ ID NO:18).

```
Veltuzumab heavy chain constant region sequence
                                    (SEQ ID NO: 18)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRW QQGNVFSCSVMHEALHNHYTQKSLSLSPGK

Rituximab heavy chain constant region sequence
                                    (SEQ ID NO: 19)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKA

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRW QQGNVFSCSVMHEALHNHYTQKSLSLSPGK
```

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113:1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | | | Heavy chain position and associated allotypes | | | | |
|---|---|---|---|---|---|---|---|
| | Complete allotype | 214 | (allo-type) | 356/358 | (allo-type) | 431 | (allo-type) |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Known Antibodies

In various embodiments, the claimed methods and compositions may utilize any of a variety of antibodies known in the art. For example, therapeutic use of hRFB4 antibody may be supplemented with one or more antibodies against other disease-associated antigens. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953; 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art (see, e.g., U.S. Pat. Nos. 7,531,327; 7,537,930; 7,608,425 and 7,785,880, the Examples section of each of which is incorporated herein by reference).

Antibodies of use may bind to various known antigens expressed in B cells or T cells, including but not limited to BCL-1, BCL-2, BCL-6, CD1a, CD2, CD3, CD4, CD5, CD7, CD8, CD10, CD11b, CD11c, CD13, CD14, CD15, CD16, CD19, CD20, CD21, CD22, CD23, CD25, CD33, CD34, CD38, CD40, CD40L, CD41a, CD43, CD45, CD47, CD55, CD56, CCD57, CD59, CD64, CD71, CD79a, CD79b, CD117, CD138, CXCR4, FMC-7 and HLA-DR.

Particular antibodies that may be of use for therapy of cancer within the scope of the claimed methods and compositions include, but are not limited to, LL1 (anti-CD74), LL2 and RFB4 (anti-CD22), RS7 (anti-epithelial glycoprotein-1 (EGP-1)), PAM4 and KC4 (both anti-mucin), MN-14 (anti-carcinoembryonic antigen (CEA, also known as CD66e), MN-15 (anti-CEACAM6), Mu-9 (anti-colon-specific antigen-p), Immu 31 (an anti-alpha-fetoprotein), TAG-72 (e.g., CC49), R1 (anti-IGF-1R), Tn, J591 or HuJ591 (anti-PSMA (prostate-specific membrane antigen), AB-PG1-XG1-026 (anti-PSMA dimer), D2/B (anti-PSMA), G250 (anti-carbonic anhydrase IX), hL243 (anti-HLA-DR), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), GA101 (anti-CD20; obinutuzumab) and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575), the text of each recited patent or application is incorporated herein by reference with respect to the Figures and Examples sections.

Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); OKT3 (anti-CDR3); anti-CD40L (UCB, Brussels, Belgium); natalizumab (anti-α4 integrin) and omalizumab (anti-IgE).

Antibody Fragments

Antibody fragments which recognize specific epitopes can be generated by known techniques. The antibody fragments are antigen binding portions of an antibody, such as F(ab)$_2$, Fab', Fab, Fv, scFv and the like. Other antibody fragments include, but are not limited to: the F(ab')$_2$ fragments which can be produced by pepsin digestion of the antibody molecule and the Fab' fragments, which can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity. In certain embodiments, the antibody fragment may be a fragment that is not an scFv fragment.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are disclosed in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991).

An antibody fragment can be prepared by known methods, for example, as disclosed by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single complementarity-determining region (CDR) is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. (See, e.g., Larrick et al., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780).

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., Molecular Cloning, A laboratory manual, $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, J Nucl Med 41:355-62; Hinton et al., 2006, J Immunol 176:346-56; Petkova et al. 2006, Int Immunol 18:1759-69; U.S. Pat. No. 7,217,797; Hwang and Foote, 2005, Methods 36:3-10; Clark, 2000, Immunol Today 21:397-402; J Immunol 1976 117:1056-60; Ellison et al., 1982, Nucl Acids Res 13:4071-79; Stickler et al., 2011, Genes and Immunity 12:213-21).

Multispecific and Multivalent Antibodies

Methods for producing bispecific antibodies include engineered recombinant antibodies which have additional cysteine residues so that they crosslink more strongly than the more common immunoglobulin isotypes. (See, e.g., FitzGerald et al, Protein Eng. 10(10):1221-1225, (1997)).

Another approach is to engineer recombinant fusion proteins linking two or more different single-chain antibody or antibody fragment segments with the needed dual specificities. (See, e.g., Coloma et al., Nature Biotech. 15:159-163, (1997)). A variety of bispecific antibodies can be produced using molecular engineering. In one form, the bispecific antibody may consist of, for example, an scFv with a single binding site for one antigen and a Fab fragment with a single binding site for a second antigen. In another form, the bispecific antibody may consist of, for example, an IgG with two binding sites for one antigen and two scFv with two binding sites for a second antigen. In alternative embodiments, multispecific and/or multivalent antibodies may be produced as DOCK-AND-LOCK™ (DNL™) complexes as described below.

In certain embodiments, a hRFB4 antibody or fragment may be administered to a patient as part of a combination of antibodies. Bispecific antibodies are preferred to administration of combinations of separate antibodies, due to cost and convenience. However, where combinations of separate antibodies provide improved safety or efficacy, the combination may be utilized. The antibodies may bind to different epitopes of the same antigen or to different antigens. Preferably, the antigens are selected from the group consisting of BCL-1, BCL-2, BCL-6, CD1a, CD2, CD3, CD4, CD5, CD7, CD8, CD10, CD11b, CD11c, CD13, CD14, CD15, CD16, CD19, CD20, CD21, CD22, CD23, CD25, CD33, CD34, CD38, CD40, CD40L, CD41a, CD43, CD45, CD47, CD55, CD56, CCD57, CD59, CD64, CD71, CD79a, CD79b, CD117, CD138, CXCR4, FMC-7 and HLA-DR. However, antibodies against other antigens of use for therapy of cancer, autoimmune diseases or immune dysfunction diseases are known in the art, as discussed below, and antibodies against any such disease-associated antigen known in the art may be utilized.

DOCK-AND-LOCK™ (DNL™)

In preferred embodiments, a bivalent or multivalent antibody is formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264. Wong and Scott, Nat. Rev. Mol. Cell Biol. 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL™ complex comprises a trimer with two DDD-linked molecules attached to one AD-linked molecule, variations in complex structure allow the formation of dimers, trimers, tetramers, pentamers, hexamers and other multimers. In some embodiments, the DNL™ complex may comprise two or more antibodies, antibody fragments or fusion proteins which bind to the same antigenic determinant or to two or more different antigens. The DNL™ complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). Thus, the four isoforms of PKA regulatory subunits are RIα, RIβ, RIIα and RIIβ. The R subunits have been isolated only as stable dimers and the dimerization domain has been shown to consist of the first 44 amino-terminal residues of RIIα or RIIβ (Newlon et al., Nat. Struct. Biol. 1999; 6:222). As discussed below, similar portions of the amino acid sequences of other regulatory subunits are involved in dimerization and docking, each located at or near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL™ complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL™ constructs of different stoichiometry may be produced and used (see, e.g., U.S. Pat. Nos. 7,550,143; 7,521,056; 7,534,866; 7,527, 787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL™ construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Structure-Function Relationships in AD and DDD Moieties

For different types of DNL™ constructs, different AD or DDD sequences may be utilized. Exemplary DDD and AD sequences are provided below.

```
DDD1
                                            (SEQ ID NO: 20)
SHIQIPPGLTELLQGYTVEVLRQQPPDLVEFAVEYFTRLREARA

DDD2
                                            (SEQ ID NO: 21)
CGHIQIPPGLTELLQGYTVEVLRQQPPDLVEFAVEYFTRLREARA

AD1
                                            (SEQ ID NO: 22)
QIEYLAKQIVDNAIQQA

AD2
                                            (SEQ ID NO: 23)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

DDD3
(SEQ ID NO: 24)
SLRECELYVQKHNIQALLKDSIVQLCTARPERPMAFLREYFERLEKEEAK

DDD3C
(SEQ ID NO: 25)
MSCGGSLRECELYVQKHNIQALLKDSIVQLCTARPERPMAFLREYFERL

EKEEAK

AD3
(SEQ ID NO: 26)
CGFEELAWKIAKMIWSDVFQQGC

In other alternative embodiments, other sequence variants of AD and/or DDD moieties may be utilized in construction of the DNL™ complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

PKA RIα
(SEQ ID NO: 27)
SLRECELYVQKHNIQALLKDVSIVQLCTARPERPMAFLREYFEKLEKEE

AK

PKA RIβ
(SEQ ID NO: 28)
SLKGCELYVQLHGIQQVLKDCIVHLCISKPERPMKFLREHFEKLEKEENR

QILA

PKA RIIα
(SEQ ID NO: 29)
SHIQIPPGLTELLQGYTVEVGQQPPDLVDFAVEYFTRLREARRQ

PKA RIIβ
(SEQ ID NO: 30)
SIEIPAGLTELLQGFTVEVLRHQPADLLEFALQHFTRLQQENER

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006, Mol Cell 24:397-408) examined the crystal structure of the AD-DDD binding interaction and concluded that the human DDD sequence contained a number of conserved amino acid residues that were important in either dimer formation or AKAP binding, underlined in SEQ ID NO:20 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding. SH<u>IQ</u>IPPG<u>LT</u>EL<u>L</u>QG<u>YT</u>V<u>E</u>V<u>L</u>RQQPPD<u>L</u>V<u>EF</u>A<u>V</u>E<u>YF</u>TR<u>L</u>REARA (SEQ ID NO:20)

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:20 are shown in Table 2. In devising Table 2, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. A limited number of such potential alternative DDD moiety sequences are shown in SEQ ID NO:32 to SEQ ID NO:51 below. The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, Proc Natl Acad Sci USA 100:4445-50).

TABLE 2

Conservative Amino Acid Substitutions in DDD1 (SEQ ID NO: 20). Consensus sequence disclosed as SEQ ID NO: 31.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | K | N |   |   |   |   |   | A | S | D |   | N | A |   | S |   | D |   |   |   | K |
|   | R |   |   |   |   |   |   |   |   |   |   |   |   |   |   |   |   |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N | N |   |   | E | L | D |   | L | D |   |   | S | K |   |   | K | D | L | K |   | L |
|   |   |   |   |   | I |   |   | I |   |   |   |   |   |   |   |   |   | I |   |   | I |
|   |   |   |   |   | V |   |   | V |   |   |   |   |   |   |   |   |   | V |   |   | V |

THIQIPPGLTELLQGYTVEVLRQQPPDLVEFAVEYFTRLREARA (SEQ ID NO: 32)

SKIQIPPGLTELLQGYTVEVLRQQPPDLVEFAVEYFTRLREARA (SEQ ID NO: 33)

SRIQIPPGLTELLQGYTVEVLRQQPPDLVEFAVEYFTRLREARA (SEQ ID NO: 34)

TABLE 2-continued

Conservative Amino Acid Substitutions in DDD1
(SEQ ID NO: 20). Consensus sequence disclosed
as SEQ ID NO: 31.

SHINIPPGLTELLQGYTVEVLRQQPPDLVEFAVEYFTRLREARA (SEQ ID NO: 35)

SHIQIPPALTELLQGYTVEVLRQQPPDLVEFAVEYFTRLREARA (SEQ ID NO: 36)

SHIQIPPGLSELLQGYTVEVLRQQPPDLVEFAVEYFTRLREARA (SEQ ID NO: 37)

SHIQIPPGLTDLLQGYTVEVLRQQPPDLVEFAVEYFTRLREARA (SEQ ID NO: 38)

SHIQIPPGLTELLNGYTVEVLRQQPPDLVEFAVEYFTRLREARA (SEQ ID NO: 39)

SHIQIPPGLTELLQAYTVEVLRQQPPDLVEFAVEYFTRLREARA (SEQ ID NO: 40)

SHIQIPPGLTELLQGYSVEVLRQQPPDLVEFAVEYFTRLREARA (SEQ ID NO: 41)

SHIQIPPGLTELLQGYTVDVLRQQPPDLVEFAVEYFTRLREARA (SEQ ID NO: 42)

SHIQIPPGLTELLQGYTVEVLKQQPPDLVEFAVEYFTRLREARA (SEQ ID NO: 43)

SHIQIPPGLTELLQGYTVEVLRNQPPDLVEFAV

TABLE 3-continued

Conservative Amino Acid Substitutions in AD1 (SEQ ID NO: 22). Consensus sequence disclosed as SEQ ID NO: 70.

```
QIEYLAKQIVDNAIQNA (SEQ ID NO: 66)

QIEYLAKQIVDNAIQQL (SEQ ID NO: 67)

QIEYLAKQIVDNAIQQI (SEQ ID NO: 68)

QIEYLAKQIVDNAIQQV (SEQ ID NO: 69)
```

Gold et al. (2006, Mol Cell 24:383-95) utilized crystallography and peptide screening to develop a SuperAKAP-IS sequence (SEQ ID NO:71), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIa. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL™ constructs. Other alternative sequences that might be substituted for the AKAP-IS AD sequence are shown in SEQ ID NO:72-74. Substitutions relative to the AKAP-IS sequence are underlined. It is anticipated that, as with the AD2 sequence shown in SEQ ID NO:23, the AD moiety may also include the additional N-terminal residues cysteine and glycine and C-terminal residues glycine and cysteine.

```
SuperAKAP-IS
                              (SEQ ID NO: 71)
QIEYVAKQIVDYAIHQA Alternative AKAP sequences
                              (SEQ ID NO: 72)
QIEYKAKQIVDHAIHQA (SEQ ID NO: 73)
QIEYHAKQIVDHAIHQA (SEQ ID NO: 74)
QIEYVAKQIVDHAIHQA
```

FIG. 2 of Gold et al. disclosed additional DDD-binding sequences from a variety of AKAP proteins, shown below.

```
RII-Specific AKAPs
                              (SEQ ID NO: 76)
AKAP-KL  PLEYQAGLLVQNAIQQAI (SEQ ID NO: 77)
AKAP79   LLIETASSLVKNAIQLSI (SEQ ID NO: 78)
AKAP-Lbc LIEEAASRIVDAVIEQVK RI-Specific AKAPs
                              (SEQ ID NO: 79)
AKAPce   ALYQFADRFSELVISEAL (SEQ ID NO: 80)
RIAD     LEQVANQLADQIIKEAT (SEQ ID NO: 81)
PV38     FEELAWKIAKMIWSDVF Dual-Specificity AKAPs
                              (SEQ ID NO: 82)
AKAP7    ELVRLSKRLVENAVLKAV (SEQ ID NO: 83)
MAP2D    TAEEVSARIVQVVTAEAV (SEQ ID NO: 84)
DAKAP1   QIKQAAFQLISQVILEAT (SEQ ID NO: 85)
DAKAP2   LAWKIAKMIVSDVMQQ
```

Stokka et al. (2006, Biochem J 400:493-99) also developed peptide competitors of AKAP binding to PKA, shown in SEQ ID NO:86-88. The peptide antagonists were designated as Ht31 (SEQ ID NO:86), RIAD (SEQ ID NO:87) and PV-38 (SEQ ID NO:88). The Ht-31 peptide exhibited a greater affinity for the RII isoform of PKA, while the RIAD and PV-38 showed higher affinity for RI.

```
                              (SEQ ID NO: 86)
Ht31  DLIEEAASRIVDAVIEQVKAAGAY (SEQ ID NO: 87)
RIAD  LEQYANQLADQIIKEATE (SEQ ID NO: 88)
PV-38 FEELAWKIAKMIWSDVFQQC
```

Hundsrucker et al. (2006, Biochem J 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 4 below. AKAPIS represents a synthetic RII subunit-binding peptide. All other peptides are derived from the RII-binding domains of the indicated AKAPs.

TABLE 4

AKAP Peptide sequences

| | Peptide Sequence |
|---|---|
| AKAPIS | QIEYLAKQIVDNAIQQA (SEQ ID NO: 22) |
| AKAPIS-P | QIEYLAKQIPDNAIQQA (SEQ ID NO: 89) |
| Ht31 | KGADLIEEAASRIVDAVIEQVKAAG (SEQ ID NO: 90) |
| Ht31-P | KGADLIEEAASRIPDAPIEQVKAAG (SEQ ID NO: 91) |
| AKAP7β-wt-pep | PEDAELVRLSKRLVENAVLKAVQQY (SEQ ID NO: 92) |
| AKAP7β-L304T-pep | PEDAELVRTSKRLVENAVLKAVQQY (SEQ ID NO: 93) |

TABLE 4-continued

AKAP Peptide sequences

| | Peptide Sequence | |
|---|---|---|
| AKAP7β-L308D-pep | PEDAELVRLSKRDVENAVLKAVQQY | (SEQ ID NO: 94) |
| AKAP7β-P-pep | PEDAELVRLSKRLPENAVLKAVQQY | (SEQ ID NO: 95) |
| AKAP7β-PP-pep | PEDAELVRLSKRLPENAPLKAVQQY | (SEQ ID NO: 96) |
| AKAP7δ-L314E-pep | PEDAELVRLSKRLVENAVEKAVQQY | (SEQ ID NO: 97) |
| AKAP1-pep | EEGLDRNEEIKRAAFQIISQVISEA | (SEQ ID NO: 98) |
| AKAP2-pep | LVDDPLEYQAGLLVQNAIQQAIAEQ | (SEQ ID NO: 99) |
| AKAP5-pep | QYETLLIETASSLVKNAIQLSIEQL | (SEQ ID NO: 100) |
| AKAP9-pep | LEKQYQEQLEEEVAKVIVSMSIAFA | (SEQ ID NO: 101) |
| AKAP10-pep | NTDEAQEELAWKIAKMIVSDIMQQA | (SEQ ID NO: 102) |
| AKAP11-pep | VNLDKKAVLAEKIVAEAIEKAEREL | (SEQ ID NO: 103) |
| AKAP12-pep | NGILELETKSSKLVQNIIQTAVDQF | (SEQ ID NO: 104) |
| AKAP14-pep | TQDKNYEDELTQVALALVEDVINYA | (SEQ ID NO: 105) |
| Rab32-pep | ETSAKDNINIEEAARFLVEKILVNH | (SEQ ID NO: 75) |

Residues that were highly conserved among the AD domains of different AKAP proteins are indicated below by underlining with reference to the AKAP IS sequence (SEQ ID NO:22). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

AKAP-IS
(SEQ ID NO: 22)
QIEYL<u>AKQ</u>IVDN<u>AIQQA</u>

Can et al. (2001, J Biol Chem 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:20. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 20)
SH*IQ*I*PP*G*L*T*E*L*L*QGY*T*V*E*V*L*R*QQ*PP*D*L*VE*FA*VE*YF*TR*L*REA*R*A

A modified set of conservative amino acid substitutions for the DDD1 (SEQ ID NO:20) sequence, based on the data of Carr et al. (2001) is shown in Table 5. The skilled artisan could readily derive alternative DDD amino acid sequences of use, as disclosed above for Table 2 and Table 3.

TABLE 5

Conservative Amino Acid Substitutions in DDD1 (SEQ ID NO: 20). Consensus sequence disclosed as SEQ ID NO: 107.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | | | N | | | | | S | | | | | | | | | | I | | | |
| | | | | | | | | | | | | | | | | | | L | | | |
| | | | | | | | | | | | | | | | | | | A | | | |

| Q | Q | P | P | D | L | V E | F | A | V E | Y | F | T | R | L | R E | A | R | A |
|---|---|---|---|---|---|---|---|---|---|---|---|---|---|---|---|---|---|---|
| | N | | | | | I D | | | | S | K | | | K | | L | | L |
| | | | | | | L | | | | | | | | | | I | | I |
| | | | | | | A | | | | | | | | | | V | | V |

The skilled artisan will realize that these and other amino acid substitutions in the DDD or AD amino acid sequences may be utilized to produce alternative species within the genus of AD or DDD moieties, using techniques that are standard in the field and only routine experimentation.

Amino Acid Substitutions

In alternative embodiments, the disclosed methods and compositions may involve production and use of proteins or peptides with one or more substituted amino acid residues. For example, the DDD and/or AD sequences used to make DNL™ constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.). Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256, 395; Stickney et al., Cancer Res. 51:6650, 1991; Yuan et al., Cancer Res. 51:3119, 1991; U.S. Pat. Nos. 6,077,499; 7,011, 812; 7,300,644; 7,074,405; 6,962,702; 7,387,772; 7,052, 872; 7,138,103; 6,090,381; 6,472,511; 6,962,702; and 6,962, 702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Targetable Constructs

In certain embodiments, targetable construct peptides labeled with one or more therapeutic or diagnostic agents for use in pre-targeting may be selected to bind to a bispecific antibody with one or more binding sites for a targetable construct peptide and one or more binding sites for a target antigen associated with a disease or condition. Bispecific antibodies may be used in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons. More usually, the targetable construct peptide will have four or more residues, such as the peptide DOTA-Phe-Lys(HSG)-Tyr-Lys(HSG)-NH$_2$ (SEQ ID NO:108), wherein DOTA is 1,4,7,10-tetraazacyclododecane1,4,7,10-tetraacetic acid and HSG is the histamine succinyl glycyl group. Alternatively, DOTA may be replaced by NOTA (1,4,7-triaza-cyclononane-1,4,7-triacetic acid), TETA (p-bromoacetamido-benzyl-tetraethylaminetetraacetic acid), NETA ([2-(4,7-biscarboxymethyl[1,4,7]triazacyclononan-1-yl-ethyl]-2-carbonylmethyl-amino]acetic acid), NODA (1,4,7-triazacylononane-1,4-diacetate) or other known chelating moieties. Chelating moieties may be used, for example, to bind to a therapeutic and or diagnostic radionuclide, paramagnetic ion or contrast agent, such as Al-$^{18}$F.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity. Exemplary methods of peptide synthesis are disclosed in the Examples below.

Where pretargeting with bispecific antibodies is used, the antibody will contain a first binding site for an antigen produced by or associated with a target tissue and a second binding site for a hapten on the targetable construct. Exemplary haptens include, but are not limited to, HSG and In-DTPA. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). However, other haptens and antibodies that bind to them are known in the art and may be used, such as In-DTPA and the 734 antibody (e.g., U.S. Pat. No. 7,534,431, the Examples section incorporated herein by reference).

Preparation of Immunoconjugates

In preferred embodiments, a therapeutic or diagnostic agent may be covalently attached to an antibody or antibody fragment to form an immunoconjugate. Where the immunoconjugate is to be administered in concentrated form by subcutaneous, intramuscular or transdermal delivery, the skilled artisan will realize that only non-cytotoxic agents may be conjugated to the antibody. Where a second antibody or fragment thereof is administered by a different route, such as intravenously, either before, simultaneously with or after the subcutaneous, intramuscular or transdermal delivery, then the type of diagnostic or therapeutic agent that may be conjugated to the second antibody or fragment thereof is not so limited, and may comprise any diagnostic or therapeutic agent known in the art, including cytotoxic agents.

In some embodiments, a diagnostic and/or therapeutic agent may be attached to an antibody or fragment thereof via a carrier moiety. Carrier moieties may be attached, for example to reduced SH groups and/or to carbohydrate side chains. A carrier moiety can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2]azide-alkyne cycloaddition reaction (Id.). For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.).

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.). Examples of such substituted cyclooctynes include difluorinated cyclooctynes, 4-dibenzocyclooctynol and azacyclooctyne (Id.). An alternative copper-free reaction involved strain-promoted alkyne-nitrone cycloaddition to give N-alkylated isoxazolines (Id.). The reaction was reported to have exceptionally fast reaction kinetics and was used in a one-pot three-step protocol for site-specific modification of peptides and proteins (Id.). Nitrones were prepared by the condensation of appropriate aldehydes with N-methylhydroxylamine and the cycloaddition reaction took place in a mixture of acetonitrile and water (Id.). These and other known click chemistry reactions may be used to attach carrier moieties to antibodies in vitro.

Agard et al. (2004, J Am Chem Soc 126:15046-47) demonstrated that a recombinant glycoprotein expressed in CHO cells in the presence of peracetylated N-azidoacetyl-mannosamine resulted in the bioincorporation of the corresponding N-azidoacetyl sialic acid in the carbohydrates of the glycoprotein. The azido-derivatized glycoprotein reacted specifically with a biotinylated cyclooctyne to form a biotinylated glycoprotein, while control glycoprotein without the azido moiety remained unlabeled (Id.). Laughlin et al. (2008, Science 320:664-667) used a similar technique to metabolically label cell-surface glycans in zebrafish embryos incubated with peracetylated N-azidoacetylgalactosamine. The azido-derivatized glycans reacted with difluorinated cyclooctyne (DIFO) reagents to allow visualization of glycans in vivo.

The Diels-Alder reaction has also been used for in vivo labeling of molecules. Rossin et al. (2010, Angew Chem Int Ed 49:3375-78) reported a 52% yield in vivo between a tumor-localized anti-TAG72 (CC49) antibody carrying a trans-cyclooctene (TCO) reactive moiety and an $^{111}$In-labeled tetrazine DOTA derivative. The TCO-labeled CC49 antibody was administered to mice bearing colon cancer xenografts, followed 1 day later by injection of $^{111}$In-labeled tetrazine probe (Id.). The reaction of radiolabeled probe with tumor localized antibody resulted in pronounced radioactivity localization in the tumor, as demonstrated by SPECT imaging of live mice three hours after injection of radiolabeled probe, with a tumor-to-muscle ratio of 13:1 (Id.). The results confirmed the in vivo chemical reaction of the TCO and tetrazine-labeled molecules.

Antibody labeling techniques using biological incorporation of labeling moieties are further disclosed in U.S. Pat. No. 6,953,675 (the Examples section of which is incorporated herein by reference). Such "landscaped" antibodies were prepared to have reactive ketone groups on glycosylated sites. The method involved expressing cells transfected with an expression vector encoding an antibody with one or more N-glycosylation sites in the CH1 or $V_\kappa$ domain in culture medium comprising a ketone derivative of a saccharide or saccharide precursor. Ketone-derivatized saccharides or precursors included N-levulinoyl mannosamine and N-levulinoyl fucose. The landscaped antibodies were subsequently reacted with agents comprising a ketone-reactive moiety, such as hydrazide, hydrazine, hydroxylamino or thiosemicarbazide groups, to form a labeled targeting molecule. Exemplary agents attached to the landscaped antibodies included chelating agents like DTPA, large drug molecules such as doxorubicin-dextran, and acyl-hydrazide containing peptides. The landscaping technique is not limited to producing antibodies comprising ketone moieties, but may be used instead to introduce a click chemistry reactive group, such as a nitrone, an azide or a cyclooctyne, onto an antibody or other biological molecule.

Modifications of click chemistry reactions are suitable for use in vitro or in vivo. Reactive targeting molecule may be formed either by either chemical conjugation or by biological incorporation. The targeting molecule, such as an antibody or antibody fragment, may be activated with an azido moiety, a substituted cyclooctyne or alkyne group, or a nitrone moiety. Where the targeting molecule comprises an azido or nitrone group, the corresponding targetable construct will comprise a substituted cyclooctyne or alkyne group, and vice versa. Such activated molecules may be made by metabolic incorporation in living cells, as discussed above.

Alternatively, methods of chemical conjugation of such moieties to biomolecules are well known in the art, and any such known method may be utilized. General methods of immunoconjugate formation are disclosed, for example, in U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.

Therapeutic and Diagnostic Agents

In certain embodiments, the antibodies or fragments thereof may be used in combination with one or more therapeutic and/or diagnostic agents. Where the agent is attached to an antibody or fragment thereof to be administered by subcutaneous, intramuscular or transdermal administration, then only non-cytotoxic agents are contemplated. Non-cytotoxic agents may include, without limitation, immunomodulators, cytokines (and their inhibitors), chemokines (and their inhibitors), tyrosine kinase inhibitors, growth factors, hormones and certain enzymes (i.e., those that do not induce local necrosis), or their inhibitors. Where the agent is co-administered either before, simultaneously with or after the subcutaneous, intramuscular or transdermal antibody formulation, then cytotoxic agents may be utilized. An agent may be administered as an immunoconjugate with a second antibody or fragment thereof, or may be administered as a free agent. The following discussion applies to both cytotoxic and non-cytotoxic agents.

Therapeutic agents may be selected from the group consisting of a radionuclide, an immunomodulator, an anti-angiogenic agent, a cytokine, a chemokine, a growth factor, a hormone, a drug, a prodrug, an enzyme, an oligonucleotide, a pro-apoptotic agent, an interference RNA, a photoactive therapeutic agent, a tyrosine kinase inhibitor, a Bruton kinase inhibitor, a sphingosine inhibitor, a cytotoxic agent, which may be a chemotherapeutic agent or a toxin, and a combination thereof. The drugs of use may possess a pharmaceutical property selected from the group consisting of antimitotic, antikinase, alkylating, antimetabolite, antibiotic, alkaloid, anti-angiogenic, pro-apoptotic agents, and combinations thereof.

Exemplary drugs may include, but are not limited to, 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celecoxib, chlorambucil, cisplatinum, Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), pro-2P-DOX, cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, paclitaxel, temazolomide (an aqueous form of DTIC), transplatinum, thalidomide, thioguanine, thiotepa, teniposide, topotecan, uracil mustard, vinorelbine, vinblastine, vincristine and *vinca* alkaloids.

Toxins may include ricin, abrin, alpha toxin, saporin, ribonuclease (RNase), e.g., onconase, DNase I, *Staphylococcal* enterotoxin-A, pokeweed antiviral protein, gelonin, diphtheria toxin, *Pseudomonas* exotoxin, and *Pseudomonas* endotoxin.

Immunomodulators may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β, -λ or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, -λ and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-23, IL-25, LIF, kit-ligand or FLT-3, angiostatin, thrombospondin, endostatin, tumor necrosis factor and lymphotoxin.

Chemokines of use include RANTES, MCAF, MIP1-alpha, MIP1-Beta and IP-10.

Radioactive isotopes include, but are not limited to $^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{227}$Th, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{227}$Th, $^{76}$Br, $^{169}$Yb, and the like.

A variety of tyrosine kinase inhibitors are known in the art and any such known therapeutic agent may be utilized. Exemplary tyrosine kinase inhibitors include, but are not limited to canertinib, dasatinib, erlotinib, gefitinib, imatinib, lapatinib, leflunomide, nilotinib, pazopanib, semaxinib, sorafenib, sunitinib, sutent and vatalanib. A specific class of tyrosine kinase inhibitor is the Bruton tyrosine kinase inhibitor. Bruton tyrosine kinase (Btk) has a well-defined role in B-cell development. Bruton kinase inhibitors include, but are not limited to, PCI-32765 (ibrutinib), PCI-45292, GDC-0834, LFM-A13 and RN486.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Corticosteroid hormones can increase the effectiveness of other chemotherapy agents, and consequently, they are frequently used in combination treatments. Prednisone and dexamethasone are examples of corticosteroid hormones.

In certain embodiments, anti-angiogenic agents, such as angiostatin, baculostatin, canstatin, maspin, anti-placenta growth factor (PlGF) peptides and antibodies, anti-vascular growth factor antibodies (such as anti-VEGF and anti-PlGF), anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, interferon-lambda, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

The therapeutic agent may comprise an oligonucleotide, such as a siRNA. The skilled artisan will realize that any siRNA or interference RNA species may be attached to an antibody or fragment thereof for delivery to a targeted tissue. Many siRNA species against a wide variety of targets are known in the art, and any such known siRNA may be utilized in the claimed methods and compositions.

Known siRNA species of potential use include those specific for IKK-gamma (U.S. Pat. No. 7,022,828); VEGF, Flt-1 and Flk-1/KDR (U.S. Pat. No. 7,148,342); Bcl2 and EGFR (U.S. Pat. No. 7,541,453); CDC20 (U.S. Pat. No. 7,550,572); transducin (beta)-like 3 (U.S. Pat. No. 7,576,196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,707); superoxide dismutase 1 (U.S. Pat. No. 7,632,938); MET proto-oncogene (U.S. Pat. No. 7,632,939); amyloid beta precursor protein (APP) (U.S. Pat. No. 7,635,771); IGF-1R (U.S. Pat. No. 7,638,621); ICAM1 (U.S. Pat. No. 7,642,349); complement factor B (U.S. Pat. No. 7,696,344); p53 (U.S. Pat. No. 7,781,575), and apolipoprotein B (U.S. Pat. No. 7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Minis Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject DNL complexes.

Exemplary siRNA species known in the art are listed in Table 6. Although siRNA is delivered as a double-stranded molecule, for simplicity only the sense strand sequences are shown in Table 6.

TABLE 6

Exemplary siRNA Sequences

| Target | Sequence | SEQ ID NO |
|--------|----------|-----------|
| VEGF R2 | AATGCGGCGGTGGTGACAGTA | SEQ ID NO: 109 |
| VEGF R2 | AAGCTCAGCACACAGAAAGAC | SEQ ID NO: 110 |

TABLE 6-continued

Exemplary siRNA Sequences

| Target | Sequence | SEQ ID NO |
|---|---|---|
| CXCR4 | UAAAAUCUUCCUGCCCACCdTdT | SEQ ID NO: 111 |
| CXCR4 | GGAAGCUGUUGGCUGAAAAdTdT | SEQ ID NO: 112 |
| PPARC1 | AAGACCAGCCUCUUUGCCCAG | SEQ ID NO: 113 |
| Dynamin 2 | GGACCAGGCAGAAAACGAG | SEQ ID NO: 114 |
| Catenin | CUAUCAGGAUGACGCGG | SEQ ID NO: 115 |
| E1A binding protein | UGACACAGGCAGGCUUGACUU | SEQ ID NO: 116 |
| Plasminogen activator | GGTGAAGAAGGGCGTCCAA | SEQ ID NO: 117 |
| K-ras | GATCCGTTGGAGCTGTTGGCGTAGTT CAAGAGACTCGCCAACAGCTCCAACT TTTGGAAA | SEQ ID NO: 118 |
| Sortilin 1 | AGGTGGTGTTAACAGCAGAG | SEQ ID NO: 119 |
| Apolipoprotein E | AAGGTGGAGCAAGCGGTGGAG | SEQ ID NO: 120 |
| Apolipoprotein E | AAGGAGTTGAAGGCCGACAAA | SEQ ID NO: 121 |
| Bcl-X | UAUGGAGCUGCAGAGGAUGdTdT | SEQ ID NO: 122 |
| Raf-1 | TTTGAATATCTGTGCTGAGAACACA GTTCTCAGCACAGATATTCTTTTT | SEQ ID NO: 123 |
| Heat shock transcription factor 2 | AATGAGAAAAGCAAAAGGTGCCCTGTCTC | SEQ ID NO: 124 |
| IGFBP3 | AAUCAUCAUCAAGAAAGGGCA | SEQ ID NO: 125 |
| Thioredoxin | AUGACUGUCAGGAUGUUGCdTdT | SEQ ID NO: 126 |
| CD44 | GAACGAAUCCUGAAGACAUCU | SEQ ID NO: 127 |
| MMP14 | AAGCCTGGCTACAGCAATATGCCTGTCTC | SEQ ID NO: 128 |
| MAPKAPK2 | UGACCAUCACCGAGUUUAUdTdT | SEQ ID NO: 129 |
| FGFR1 | AAGTCGGACGCAACAGAGAAA | SEQ ID NO: 130 |
| ERBB2 | CUACCUUUCUACGGACGUGdTdT | SEQ ID NO: 131 |
| BCL2L1 | CTGCCTAAGGCGGATTTGAAT | SEQ ID NO: 132 |
| ABL1 | TTAUUCCUUCUUCGGGAAGUC | SEQ ID NO: 133 |
| CEACAM1 | AACCTTCTGGAACCCGCCCAC | SEQ ID NO: 134 |
| CD9 | GAGCATCTTCGAGCAAGAA | SEQ ID NO: 135 |
| CD151 | CATGTGGCACCGTTTGCCT | SEQ ID NO: 136 |
| Caspase 8 | AACTACCAGAAAGGTATACCT | SEQ ID NO: 137 |
| BRCA1 | UCACAGUGUCCUUUAUGUAdTdT | SEQ ID NO: 138 |
| p53 | GCAUGAACCGGAGGCCCAUU | SEQ ID NO: 139 |
| CEACAM6 | CCGGACAGTTCCATGTATA | SEQ ID NO: 140 |

The skilled artisan will realize that Table 6 represents a very small sampling of the total number of siRNA species known in the art, and that any such known siRNA may be utilized in the claimed methods and compositions.

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{18}F$, $^{52}Fe$, $^{110}In$, $^{111}In$, $^{177}Lu$, $^{52}Fe$, $^{62}Cu$, $^{64}Cu$, $^{67}Cu$, $^{67}Ga$, $^{68}Ga$, $^{86}Y$, $^{90}Y$, $^{89}Zr$, $^{94m}Tc$, $^{94}Tc$, $^{99m}Tc$, $^{120}I$, $^{123}I$, $^{124}I$, $^{125}I$, $^{131}I$, $^{154-158}Gd$, $^{32}P$, $^{11}C$, $^{13}N$, $^{15}O$, $^{186}Re$, $^{188}Re$, $^{51}Mn$, $^{52m}Mn$, $^{55}Co$, $^{72}As$, $^{75}Br$, $^{76}Br$, $^{82m}Rb$, $^{83}Sr$, or other gamma-, beta-, or positron-emitters.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III).

Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Methods of Administration

The subject antibodies and immunoglobulins in general may be formulated to obtain compositions that include one or more pharmaceutically suitable excipients, surfactants, polyols, buffers, salts, amino acids, or additional ingredients, or some combination of these. This can be accomplished by known methods to prepare pharmaceutically useful dosages, whereby the active ingredients (i.e., the labeled molecules) are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parenteral injection, more preferably by subcutaneous, intramuscular or transdermal delivery. Other forms of parenteral administration include intravenous, intraarterial, intralymphatic, intrathecal, intraocular, intracerebral, or intracavitary injection. In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hanks' solution. Nonaqueous excipients such as fixed oils and ethyl oleate may also be used. An alternative excipient is 5% dextrose in saline. The excipient may contain minor amounts of additives such as substances that enhance isotonicity and chemical stability, including buffers and preservatives.

Formulated compositions comprising antibodies can be used for subcutaneous, intramuscular or transdermal administration. Compositions can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The formulation thereof should be in a solution having a suitable pharmaceutically acceptable buffer such as phosphate, TRIS (hydroxymethyl) aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as mannitol, trehalose, sorbitol, glycerol, albumin, a globulin, a detergent, a gelatin, a protamine or a salt of protamine may also be included.

The dosage of an administered antibody for humans will vary depending upon such factors as the patient's age, weight, height, sex, general medical condition and previous medical history. Typically, it is desirable to provide the recipient with a dosage of antibody that is in the range of from about 1 mg to 600 mg as a single infusion or single or multiple injections, although a lower or higher dosage also may be administered. Typically, it is desirable to provide the recipient with a dosage that is in the range of from about 50 mg per square meter ($m^2$) of body surface area or 70 to 85 mg of the antibody for the typical adult, although a lower or higher dosage also may be administered. Examples of dosages of antibodies that may be administered to a human subject are 1 to 1,000 mg, more preferably 1 to 70 mg, most preferably 1 to 20 mg, although higher or lower doses may be used. Dosages may be repeated as needed, for example, once per week for 4-10 weeks, preferably once per week for 8 weeks, and more preferably, once per week for 4 weeks. It may also be given less frequently, such as every other week for several months, or more frequently, such as twice weekly or by continuous infusion.

More recently, subcutaneous administration of veltuzumab has been given to NHL patients in 4 doses of 80, 160 or 320 mg, repeated every two weeks (Negrea et al., 2011, Haematologica 96:567-73). Only occasional, mild to moderate and transient injection reactions were observed, with no other safety issues (Id.). The objective response rate (CR+CRu+PR) was 47%, with a CR/CRu (complete response) rate of 24% (Id.). Interestingly, the 80 mg dosage group showed the highest percentage of objective response (⅔, 67%), with one of three patients showing a complete response (Id.). Four out of eight objective responses continued for 60 weeks (Id.). All serum samples evaluated for HAHA were negative (Id.). Although the low sample population reported in this study precludes any definitive conclusions on optimal dosing, it is apparent that therapeutic response was observed at the lowest dosage tested (80 mg).

In certain alternative embodiments, the antibody may be administered by transdermal delivery. Different methods of transdermal delivery are known in the art, such as by transdermal patches or by microneedle devices, and any such known method may be utilized. In an exemplary embodiment, transdermal delivery may utilize a delivery device such as the 3M hollow Microstructured Transdermal System (hMTS) for antibody based therapeutics. The hMTS device comprises a 1 $cm^2$ microneedle array consisting of 18 hollow microneedles that are 950 microns in length, which penetrate approximately 600-700 microns into the dermal layer of the skin where there is a high density of lymphatic channels. A spring-loaded device forces the antibody composition from a fluid reservoir through the microneedles for delivery to the subject. Only transient erythema and edema at the injection site are observed (Burton et al., 2011, Pharm Res 28:31-40). The hMTS device is not perceived as a needle injector, resulting in improved patient compliance.

In alternative embodiments, transdermal delivery of peptides and proteins may be achieved by (1) coadministering with a synthetic peptide comprising the amino acid sequence of ACSSSPSKHCG (SEQ ID NO:141) as reported by Chen et al. (Nat Biotechnol 2006; 24: 455-460) and Carmichael et al. (Pain 2010; 149:316-324); (2) coadministering with arginine-rich intracellular delivery peptides as reported by Wang et al. (BBRC 2006; 346: 758-767); (3) coadminstering with either AT1002 (FCIGRLCG, SEQ ID NO:142) or Tat (GRKKRRNRRRCG, SEQ ID NO:143) as reported by Uchida et al. (Chem Pharm Bull 2011; 59:196); or (4) using an adhesive transdermal patch as reported by Jurynczyk et al (Ann Neurol 2010; 68:593-601). In addition, transdermal delivery of negatively charged drugs may be facilitated by combining with the positively charged, pore-forming magainin peptide as reported by Kim et al. (Int J Pharm 2008; 362:20-28).

In preferred embodiments where the antibody is administered subcutaneously, intramuscularly or transdermally in a concentrated formulation, the volume of administration is preferably limited to 3 ml or less, more preferably 2 ml or less, more preferably 1 ml or less. The use of concentrated antibody formulations allowing low volume subcutaneous, intramuscular or transdermal administration is preferred to the use of more dilute antibody formulations that require specialized devices and ingredients (e.g., hyaluronidase) for subcutaneous administration of larger volumes of fluid, such as 10 ml or more. The subcutaneous, intramuscular or transdermal delivery may be administered as a single administration to one skin site or alternatively may be repeated one or more times, or even given to more than one skin site in one therapeutic dosing session. However, the more concentrated the formulation, the lower the volume injected and the fewer injections will be needed for each therapeutic dosing.

Methods of Use

In preferred embodiments, the hRFB4 antibody or fragment thereof is of use for therapy of cancer. Examples of cancers include, but are not limited to, lymphoma, leukemia and lymphoid malignancies. In preferred embodiments, the antibodies or fragments thereof are of use to treat hematopoietic cancers. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: acute childhood lymphoblastic leukemia, acute lymphoblastic leukemia, acute lymphocytic leukemia, acute myeloid leukemia, adult acute lymphocytic leukemia, adult acute myeloid leukemia, adult Hodgkin's disease, adult Hodgkin's lymphoma, adult lymphocytic leukemia, adult non-Hodgkin's lymphoma, AIDS-related lymphoma, AIDS-related malignancies, central nervous system (primary) lymphoma, central nervous system lymphoma, childhood acute lymphoblastic leukemia, childhood acute myeloid leukemia, childhood Hodgkin's disease, childhood Hodgkin's lymphoma, childhood lymphoblastic leukemia, childhood non-Hodgkin's lymphoma, chronic lymphocytic leukemia, chronic myelogenous leukemia, cutaneous T-cell lymphoma, hairy cell leukemia, Hodgkin's disease, Hodgkin's lymphoma, hypergammaglobulinemia, lymphoproliferative disorders, macroglobulinemia, multiple myeloma, multiple myeloma/plasma cell neoplasm, myelodysplastic syndrome, myelogenous leukemia, myeloid leukemia, myeloproliferative disorders, non-Hodgkin's lymphoma during pregnancy, plasma cell neoplasm/multiple myeloma, primary central nervous system lymphoma, T-cell lymphoma, Waldenstrom's macroglobulinemia, and any other hyperproliferative disease.

The methods and compositions described and claimed herein may be used to detect or treat malignant or premalignant conditions. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, and Waldenstrom's macroglobulinemia.

Exemplary autoimmune diseases include acute idiopathic thrombocytopenic purpura, chronic immune thrombocytopenia, dermatomyositis, Sydenham's chorea, myasthenia gravis, systemic lupus erythematosus, lupus nephritis, rheumatic fever, polyglandular syndromes, bullous pemphigoid, pemphigus vulgaris, juvenile diabetes mellitus, Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis and fibrosing alveolitis.

Kits

Various embodiments may concern kits containing components suitable for treating diseased tissue in a patient. Exemplary kits may contain at least one hRFB4 antibody or fragment thereof as described herein. A device capable of delivering the kit components by injection, for example, a syringe for subcutaneous injection, may be included. Where transdermal administration is used, a delivery device such as hollow microneedle delivery device may be included in the kit. Exemplary transdermal delivery devices are known in the art, such as 3M's hollow Microstructured Transdermal System (hMTS), and any such known device may be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Alternatively, the hRFB4 antibody or fragment may be delivered and stored as a liquid formulation. Other containers that may be used include, but are not limited to, a pouch, tray, box, tube, or the like. Kit components may be packaged and maintained sterilely within the containers. Another component that can be included is instructions to a person using a kit for its use.

EXAMPLES

Example 1

Production and Use of Humanized RFB4 Antibody

The cDNA sequences encoding humanized RFB4 were designed by inserting the RFB4 CDR sequences into the FR and constant regions of the hLL2 antibody (see, e.g., U.S. Pat. No. 5,789,554, the Figures and Examples section of which is incorporated herein by reference). DNA sequences comprising the VH (XhoI—Hind III) and VK (Xba I—Bam HI) were synthesized by Genscript and engineered into the Ck-AD2-hLL2-IgG-pdHL2 vector in two steps.

```
hRFB4-V_K
                                          (SEQ ID NO: 144)
tctagacacaggacctcaccatgggatggagctgtatcatcctcttcttg gtagcaacagctacaggtaaggggctcacagtagcaggcttgaggtctgg acatatatgggtgacaatgacatccactttgcctttctctccacaggt gtccactccgacatccagctgacccagtctccatcatctctgagcgcatc tgttggagatagggtcactattagctgtcgagcaagtcaggacattagca attatctgaactggtaccagcagaaaccagggaaagcacctaaactgctg atctactacacatcaatattacactccggtgtcccttcgcgattctctgg cagcggatctgggacagattatactttcaccatcagctctcttcaaccag aagacattgcaacatattattgtcaacagggtaatacgcttccgtggacg ttcggtggagggaccaaggtgcagatcaaacgtgagtagaatttaaactt tgcttcctcagttggatcc hRFB4-V_H
                                          (SEQ ID NO: 145)
ctcgagcacacaggacctcaccatgggatggagctgtatcatcctcttct tggtagcaacagctacaggtaaggggctcacagtagcaggcttgaggtct ggacatatatgggtgacaatgacatccactttgcctttctctccacag gtgtccactccaggtccagctggtccaatcaggggctgaagtcaagaaa cctgggtcatcagtgaaggtctcctgcaaggcttctggcttcacctttag tatctatgacatgtcttgggtcaggcaggcacctggacagggtctggaat gggtcgcatacattagtagtggtggtggtaccacctactatccagacact gtgaagggccgattcacaataactgcagacgaatccaccaatacagccta catggagctgagcagcctgaggtctgaggacacggcattttattttgtg caagacatagtggctacggtagtagctacggggtttgtttgcttactgg ggccaaggcaccctggtcaccgtctcctcaggtgagtccttacaacctct ctcttctattcagcttaaatagattttactgcatttgttgggggggaaat gtgtgtatctgaatttcaggtcatgaaggactagggacaccttgggagtc agaaagggtcattgggaagctt
```

Step 1

The hRFB4-VL sequence (519 bp) was excised from pUC57 by digestion with Xba I and Bam HI and ligated into $C_k$-AD2-IgG-hLL2 vector fragment prepared by digestion with the same enzymes. This resulted in an intermediate vector $C_k$-AD2-hRFB4-$V_k$/hLL2 $V_H$-pdHL2. The correct clones were identified by restriction digest with Ssp I. (Correct: 7308, 1673 and 899 by (three cuts). Original vector: 8195 and 1673 by (two cuts).)

Step 2

The hRFB4-$V_H$ sequence (672 bp) was excised from its pUC57 vector by digestion with Xho I and Hind III and ligated into the intermediate vector $C_k$-AD2-hRFB4-$V_k$/hLL2 $V_H$-pdHL2 prepared by digestion with the same enzymes. The final vector was confirmed by restriction digest with Kpn I. (Correct: 7101 by and 2779 bp. Intermediate vector: 10 kb vector band only (single cut).)

The hRFB4 antibody was prepared as described above, resulting in a humanized anti-CD22 antibody with variable region sequences as shown in FIG. 1A and FIG. 1B (SEQ ID NO:7 and SEQ ID NO:8). After expression, the binding affinity or CD22+ Daudi cells was compared to that of the hLL2 antibody, comprising the same FR and constant region sequences but different CDR sequences, and to the chimeric RFB4 antibody, comprising the same CDR sequences but different FR and constant region sequences. Surprisingly, the hRFB4 antibody showed a 10-fold higher binding affinity for CD22 than hLL2 (0.2 vs. 2 nM), as shown in FIG. 2. The substantially higher affinity compared to hLL2 is particularly surprising in view of earlier reports that a chimeric RFB4 antibody exhibited approximately the same affinity for CD22 as epratuzumab (hLL2) (Li et al., 2012, mAbs 4:256-66).

A direct comparison of binding affinities of the IgG forms of hLL2, cRFB4 and hRFB4 is shown in FIG. 3. Daudi cells ($1\times10^6$ cells) were incubated with 200 µl of a sample containing varying concentrations of hLL2, hRFB4, or cRFB4 in FACS buffer (PBS, 1% BSA) for 45 min at 4° C. in FACSCAN™ tubes. Cells were pelleted at 200 g at 4° C. for 5 min and washed twice with 500 µl of FACS buffer. For detection of bound antibodies, cells were incubated with saturating amounts of FITC conjugated F(ab) Fragment goat anti-Human IgG, Fc specific (13 µg/ml; Jackson Immuno Research, West Grove, Pa.) for 45 min at 4° C. and washed in with 500 µl of FACS buffer. Stained cells were analyzed on a FACSCAN™ Flow Cytometer (BD Bioscience, San Jose, Calif.), and median fluorescence intensity (MFI) was calculated using CELLQUEST™ software (BD Bioscience). Each sample was measured in triplicate, with the standard deviations shown in the figure as bars.

As indicated in FIG. 3, the binding affinities of cRFB4 and hRFB4 IgG for Daudi cells were approximately equal. The affinity of hRFB4 IgG for Daudi cells was 19-fold higher than the hLL2 IgG in this assay. These results confirm the surprisingly higher affinity for CD22 of hRFB4 in comparison with hLL2.

Figure 4A:
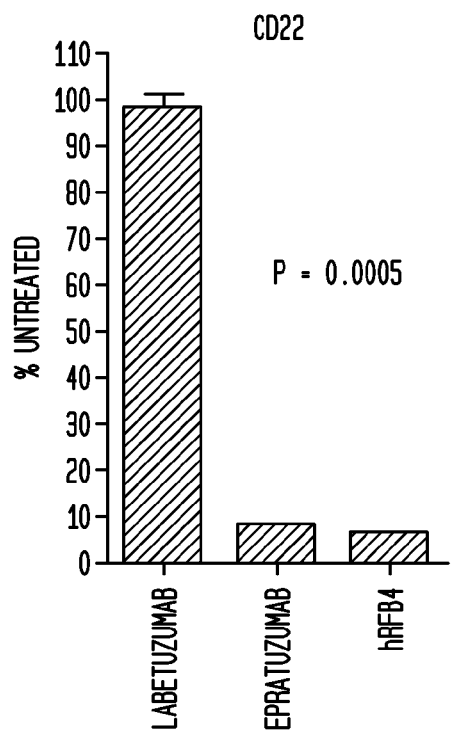
FIG. 4A. Trogocytosis induced by anti-CD22 antibodies. Comparison of the mean fluorescence intensity for CD22 on B cells following overnight treatment of PBMCs with epratuzumab, hRFB4 or labetuzumab (anti-CEACAM5 as an isotype control). Results are shown as the percent of the signal obtained from untreated cells. Error bars, St. Dev. These results demonstrate hRFB4 is as capable of mediating trogocytosis as hLL2.
Figure 4B:
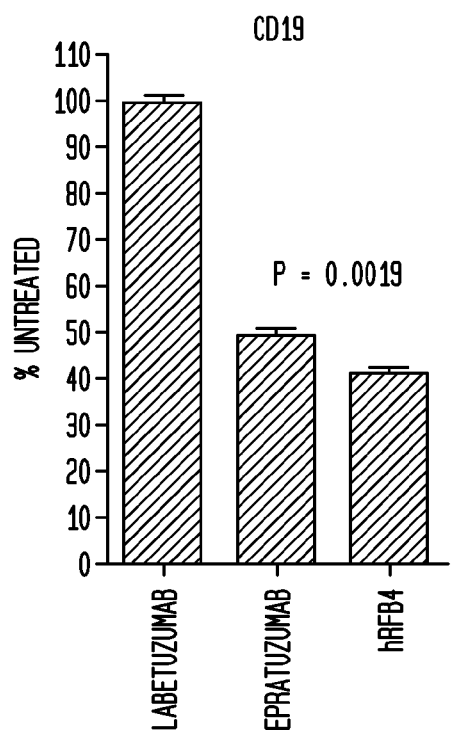
FIG. 4B. Trogocytosis induced by anti-CD22 antibodies. Comparison of the mean fluorescence intensity for CD19 on B cells following overnight treatment of PBMCs with epratuzumab, hRFB4 or labetuzumab (anti-CEACAM5 as an isotype control). Results are shown as the percent of the signal obtained from untreated cells. Error bars, St. Dev. These results demonstrate hRFB4 is as capable of mediating trogocytosis as hLL2.
Figure 4C:
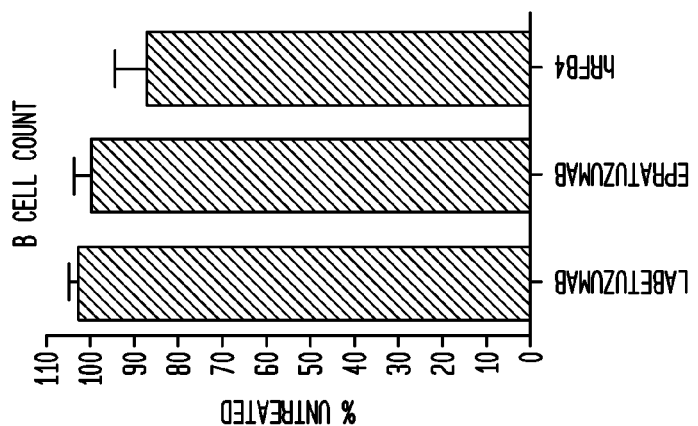
FIG. 4C. Trogocytosis induced by anti-CD22 antibodies. Comparison of the mean fluorescence intensity for CD21 on B cells following overnight treatment of PBMCs with epratuzumab, hRFB4 or labetuzumab (anti-CEACAM5 as an isotype control). Results are shown as the percent of the signal obtained from untreated cells. Error bars, St. Dev. These results demonstrate hRFB4 is as capable of mediating trogocytosis as hLL2.
Figure 4D:
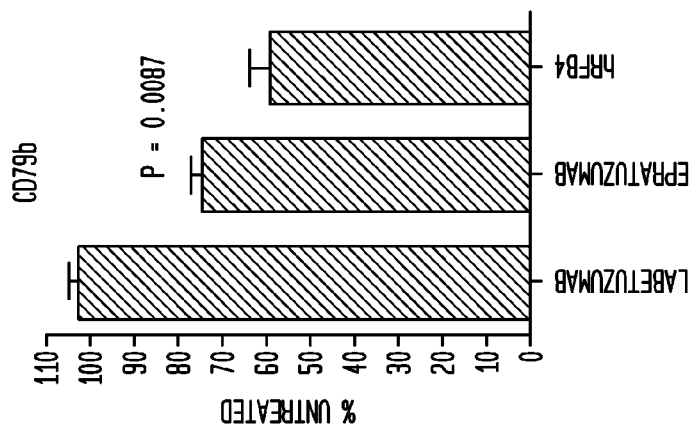
FIG. 4D. Trogocytosis induced by anti-CD22 antibodies. Comparison of the mean fluorescence intensity for CD79b on B cells following overnight treatment of PBMCs with epratuzumab, hRFB4 or labetuzumab (anti-CEACAM5 as an isotype control). Results are shown as the percent of the signal obtained from untreated cells. Error bars, St. Dev. These results demonstrate hRFB4 is as capable of mediating trogocytosis as hLL2.
Figure 4E:
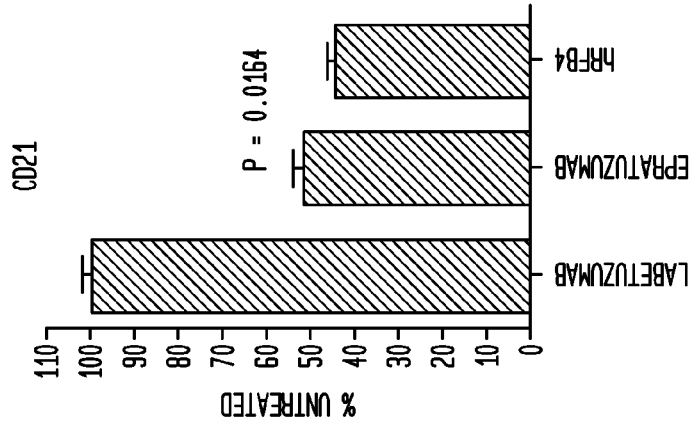
FIG. 4E. At the same concentrations as used to induce trogocytosis, none of the tested antibodies induced a substantial reduction of B cell count.

As discussed in the Example below, the hLL2 antibody induces trogocytosis of BCR-associated antigens from the surface of B lymphocytes. The efficacy of hRFB4 at inducing trogocytosis was compared to hLL2 and an isotype control hMN-14 antibody (FIG. 4A-4D). The hRFB4 antibody was more efficacious than the hLL2 antibody at inducing trogocytosis (FIG. 4A-4D). None of the tested antibodies induced any substantial reduction in the number of B cells (FIG. 4E). These results are summarized in FIG. 5.

A dose-response curve for trogoycytosis of CD19 and CD22 (FIG. 6A and FIG. 6B) shows that the maximal level of trogocytosis was induced at 1 ng/mL of hRFB4, but required 10 ng/ml of hLL2.

hLL2 has demonstrated efficacy against hematopoietic cancers, immune system dysfunction and autoimmune disease, by a mechanism involving trogocytosis of BCR-associated antigens such as CD19, CD20, CD21, CD22 and CD79b. It is demonstrated herein that hRFB4 is significantly more potent at inducing trogocytosis of the same BCR-associated antigens from B cells. The data show that hRFB4 is a potent therapeutic agent for use against hematopoietic cancers, immune system dysfunction and autoimmune disease.

Example 2

Epratuzumab-Induced Trogocytosis of BCR-Response Modulating Proteins Ex Vivo

The humanized anti-CD22 antibody, epratuzumab, has demonstrated therapeutic activity in clinical trials of patients with non-Hodgkin lymphoma (NHL), acute lymphoblastic leukemia, primary Sjögren's syndrome, and systemic lupus erythematosus (SLE). Thus, epratuzumab offers a promising option for CD22-targeted immunotherapy of B-cell lymphomas and autoimmune diseases. However, its mechanism of action (MOA) remains incompletely understood to-date. Because epratuzumab has modest, but significant, antibody-dependent cell-mediated cytotoxicity and negligible complement-dependent cytotoxicity when evaluated in vitro, and its moderate depletion of circulating B cells in patients (35% on average) may be overestimated due to use of $CD19^+$ cells to measure B cells by flow cytometry, the therapeutic action of epratuzumab in vivo may not result from B-cell depletion. We investigated whether ligation of epratuzumab to CD22 could modulate other surface molecules on B cells. In particular, we focused on those surface molecules involved in regulating antigen-specific B-cell receptor (BCR) signaling, since modulation of such molecules may lead to altered B-cell functions that ultimately mitigate symptoms of autoimmune or other diseases. With regard to its function of killing malignant B cells expressing CD22, our studies have shown that these effects are more related to the BCR signaling pathway than effector-cell function.

Epratuzumab induced a substantial reduction of CD22, along with CD19, CD21, CD20, and CD79b, on the surface of B cells in peripheral blood mononuclear cells (PBMCs) obtained from normal donors or lupus patients, and three NHL Burkitt cell lines (Daudi, Raji, and Ramos) spiked into normal PBMCs. The intriguing observation that only CD22, but not other surface markers, was appreciably decreased by epratuzumab in isolated NHL cells prompted us to assess the role of FcγR-bearing effector cells, with the finding that epratuzumab effectively mediates trogocytosis [a process whereby cells binding to antigen-presenting cells extract surface molecules from these cells and express them on their own surface] of multiple surface proteins from B cells to monocytes, NK cells, and neutrophils. This mechanism of action may explain the limited effectiveness of high doses of epratuzumab compared to lower doses in patients with SLE.

Peripheral blood mononuclear cells (PBMCs) obtained from healthy donors were incubated overnight (16-24 h) with 10 μg/mL of either epratuzumab or an isotype control mAb (hMN-14) and the relative levels of various antigens on the surface of the B cells were analyzed by flow cytometry. PBMCs from heparinized whole blood of normal donors were isolated by density gradient centrifugation on UNI-SEP tubes (Novamed Ltd, Israel). PBMCs were reconstituted in RPMI media supplemented with 10% heat inactivated fetal bovine serum and plated at a cell density of $1.5\times10^6$/mL in non-tissue culture treated 48-well plates. Epratuzumab or hMN-14 were added to triplicate wells at a final concentration of 10 μg/mL and incubated overnight (16-20 h) before staining with fluorescent-labeled primary antibodies (Biolegend) following the manufacturers suggested protocols. Stained cells were analyzed by flow cytometry on a FACSCALIBUR® (BD Biosciences) using Flowjo (V7.6.5) software. Initially, the lymphocyte population was gated by side vs. forward scattering, and B cells were further gated from this population with the CD19 signal. The mean fluorescence intensity (MFI), obtained with fluorochrome-conjugated antibodies to various cell surface antigens, on the gated B cells was calculated following treatment with epratuzumab, hMN-14 or without antibody. PBMCs from 16 healthy donors were assessed in various experiments.

Treatment with the control mAb (hMN-14) did not affect the levels of any of the tested proteins and resulted in MFI measurements that were very similar to untreated samples. Alternatively, epratuzumab significantly reduced the levels of key BCR-regulating proteins, including CD22, CD19, CD21 and CD79b, which were reduced to 10, 50, 52 and 70%, respectively, of the level of untreated or control mAb (data not shown). CD20 (82%) and CD62L (73%) also were reduced, but to a lesser extent. Other surface proteins including CD27 (on $CD27^+$ B cells), CD40, CD44, CD45, P7 integrin and LFA-1 (CD11a and CD18) were affected minimally (<10% change) by epratuzumab. $CD27^-$ naive B cells were more responsive to epratuzumab compared to $CD27^+$ memory B cells, as shown with PBMCs as shown for CD19 from 3 different healthy donors (not shown). CD22, CD21 and CD79b were also reduced to a greater extent on $CD27^-$ cells (not shown). The effect was essentially complete within a few hours. The reductions in surface CD19 and CD21 were not significantly different following 2-h or overnight treatment (not shown).

We propose that the consequences of losing CD19 from B cells are as follows. BCR activation upon encountering membrane-bound antigen involves the initial spreading and the subsequent formation of microclusters. Because CD19 is critical for mediating B-cell spreading, CD19-deficient B cells are unable to gather sufficient antigen to trigger B-cell activation. In addition, loss of CD19 on B cells may severely affect the ability of B cells to become activated in response to T cell-dependent antigens. Thus, loss of CD19 (and possibly other BCR markers and cell-adhesion molecules) on target B cells exposed to anti-CD22 antibody may incapacitate such B cells and render them unresponsive to activation by T cell-dependent antigen. In summary, anti-CD22 antibody inactivates B cells via the loss of CD19, other BCR constituents, and cell-adhesion molecules that are involved in sustaining B-cell survival, leading to therapeutic control in B-cell-mediated autoimmune diseases.

It has been shown with rituximab administered to chronic lymphocytic leukemia cells that too much antibody results in removal of complexes of rituximab-CD20 from the leukemia cells by trogocytosis to monocytes, and can enable these malignant cells to escape the effects of the antibody by antigenic modulation. It was then found that reducing the dose of therapeutic antibody could limit the extent of trogocytosis and improve the therapeutic effects (Herrera et al., 2006). Based on our present findings, a similar process of antigen shaving (trogocytosis) by anti-CD22 or anti-CD20 antibodies that extends beyond the respective targeted antigens can be implicated in the therapy with RFB4 or rituximab (or the humanized anti-CD20 mAb, veltuzumab).

Example 3

Effect of Various B Cell-Targeting Antibodies

Figure 8:
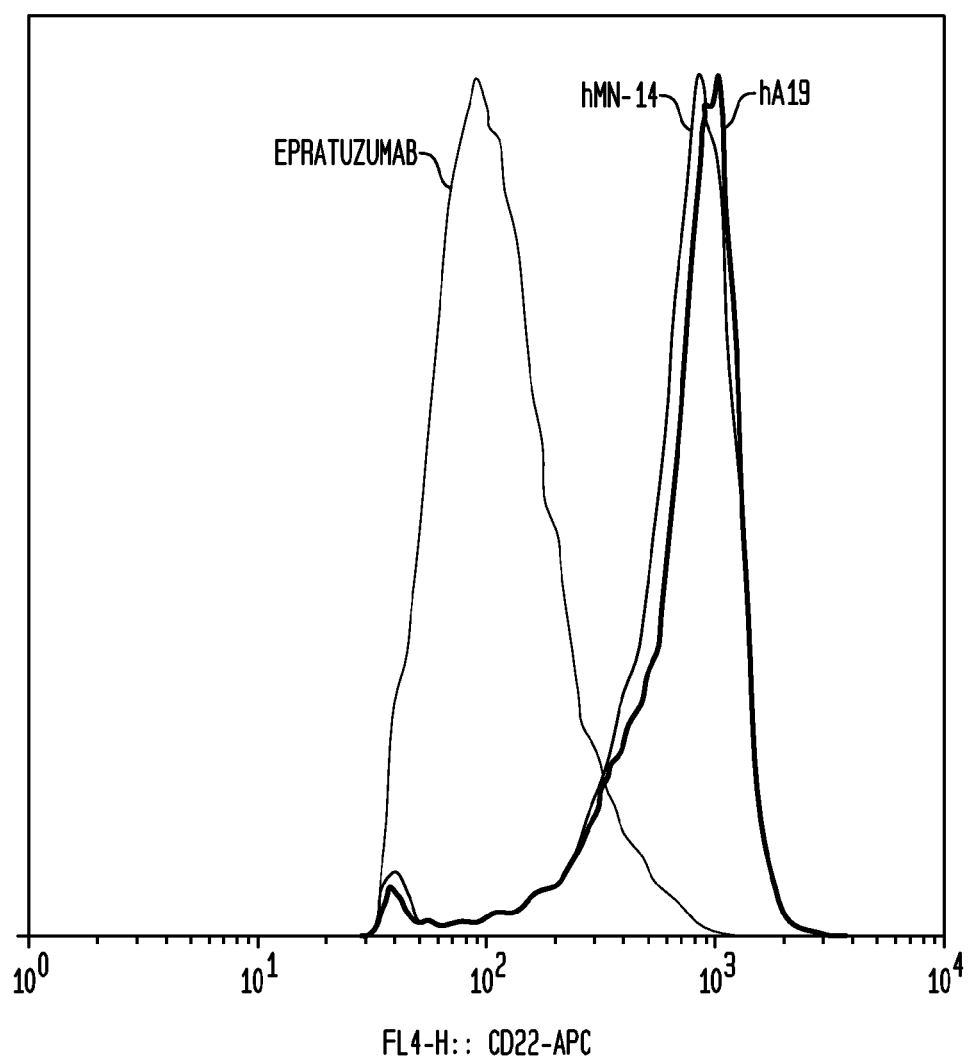
FIG. 8. Histogram showing CD22 levels on B cells gated from PBMCs of healthy donors following overnight treatment with 10 μg/mL epratuzumab, hA19 (anti-CD19) or isotype control (hMN-14).
Figure 9:
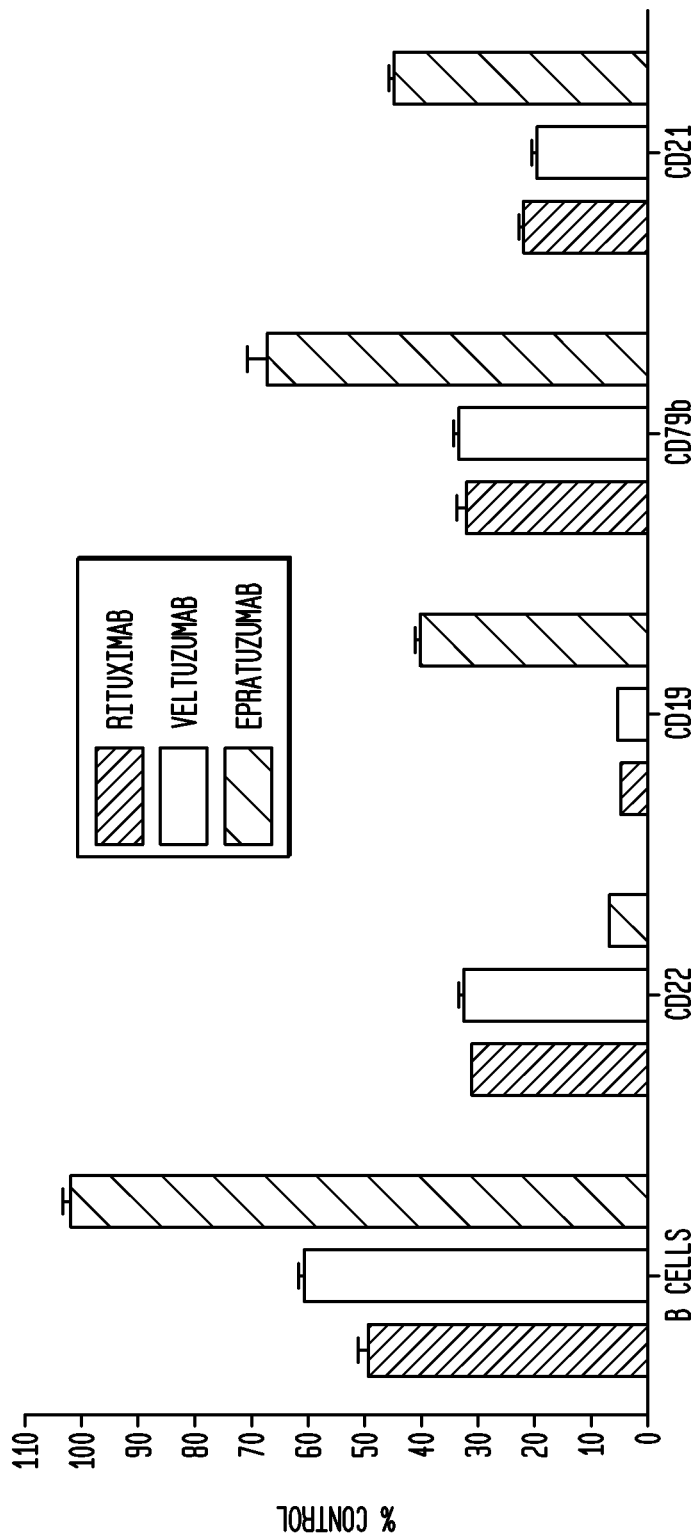
FIG. 9. Fresh PBMCs isolated from healthy donors were treated overnight with epratuzumab, veltuzumab or rituximab. The relative B cell count (B cells) and levels of CD19, CD22, CD21 and CD79b following treatment is shown as the % mean fluorescence intensity of the isotype control (hMN-14) treatment at the same protein concentration. Error bars, Std. Dev.

Compared to epratuzumab, a humanized antibody to CD19 (hA19) moderately reduced the level of CD22 on B cells (66% of control) within PBMCs (FIG. 8). Although treatment with hA19 precluded measurement of CD19, that hA19 lowered the level of CD21, to a similar level as epratuzumab, suggests that a concomitant reduction in CD19 also is likely. The CD20 targeting mAbs rituximab and veltuzumab each diminished CD19, CD21 and CD79b to a greater extent than epratuzumab (FIG. 9). Rituximab also reduced CD22, but to a lesser extent than epratuzumab. Notably, rituximab and veltuzumab (at 10 μg/mL) reduced the B cell count by 50%, and 40%, where epratuzumab did not cause significant B cell depletion, either at 10 μg/mL or 1 mg/mL. Unlike rituximab, which reduces the same antigens via trogocytosis, but also potently kills B cells, epratuzumab does not deplete B cells ex vivo.

Example 4

The Fc is Required for Trogocytosis

A F(ab')$_2$ fragment of RFB4, which is prepared by pepsin digestion, reduces CD22 moderately (45% control), compared to the full IgG (10% control), and has no effect on CD19, CD21 and CD79b. The loss of CD22 can be attributed to internalization of the antibody/antigen complex, which is a well established phenomenon, and not due to trogocytosis. That CD19, CD21 and CD79 are not affected by the F(ab')$_2$ indicates that no trogocytosis is induced by the Fc-lacking antibody fragment. A similar finding is observed when PBMCs from lupus patients are used instead of from healthy donors.

Example 5

Effector Cells are Required for RFB4-Induced Trogocytosis

B cell lymphoma cell lines are used as "isolated B cells" that are evaluated for RFB4 induced trogocytosis. In vitro, RFB4 induces an intermediate reduction (33% control) of CD22 on the surface of isolated Daudi Burkitt lymphoma cells, and does not affect the levels of other markers. In an ex vivo setting, where Daudi are spiked into PBMCs from a healthy donor, RFB4 minimizes CD22 (<5% control) and significantly reduces CD19 (28% control), CD21 (40% control), CD79b (72% control) and surface IgM (73% control). Similar results are obtained with Raji lymphoma cells, where CD19, CD21 and CD79b are diminished by RFB4 only in the presence of PBMCs. The addition of a crosslinking second antibody results in only a modest reduction of CD19, CD21 and CD79b. That the effect only is observed in the presence of PBMCs, and is not accomplished in the presence of PBMCs with a F(ab')$_2$ fragment or with a crosslinking second antibody in place of PBMCs, indicates that effector cells bearing Fc receptors are involved in the RFB4-induced trogocytosis process.

Example 6

Monocytes, but not T Cells can Modulate RFB4-Induced Trogocytosis

Combined, T cells and monocytes comprise approximately 70-80% of the total PBMCs. The ability of PBMC fractions, which are depleted of either T cells or monocytes using MACS® separation technology (Miltenyi Biotec) with magnetically labeled microbeads in an LS or MS column, are evaluated for RFB4-induced reduction of CD22 and CD19 on Daudi and normal B cells. For this experiment the ratio of total effector cells to Daudi is held constant. Therefore, removal of a specific cell type results in increased numbers of the remaining cell types. Depletion of T cells is only 50% efficient; however, this results in a 10% increase in monocytes and other cell types. The T-cell-depleted PBMCs are significantly more active than total PBMCs, indicating that T cells are not involved. Purified T cells are not capable of affecting the RFB4-induced reduction of CD19 or CD21 on Daudi. Conversely, depletion of monocytes, which is 99% efficient, significantly dampens the reduction of both CD19 and CD22 on either Daudi or B cells, implicating the involvement of monocytes. That there is appreciable reduction of CD19 with the monocyte-depleted PBMCs, suggests the participation of additional cell types.

In a subsequent experiment, purified monocytes (94%) induce a similar decrease in CD19 as the whole PBMCs, whereas the remaining monocyte-depleted PBMCs have minimal effect, comparable to the levels measured without effector cells. A similar pattern is observed for CD22. The results support the key role of monocytes among PBMCs.

Example 7

RFB4-Induced Trogocytosis with Monocytes

Trogocytosis involves the transfer of membrane components from one cell to another. To determine if the loss of surface antigen on B cells is due to their transfer to effector cells (trogocytosis), Daudi cells are mixed with PBMCs, purified monocytes or monocyte-depleted PBMCs, and treated with RFB4 or the isotype control for 1 h. Daudi, monocyte and lymphocyte populations are gated by forward vs. side scattering. When mixed with Daudi cells and treated with RFB4, but not the isotype control mAb, purified monocytes (CD14 positive cells) stain positive for CD22 (56.6% positive) and CD19 (52.4% positive), with 44% positive for both. Treatment with an isotype control mAb result in only 1.6% double positive monocytes. The monocytes are further gated into CD14$^{++}$ (~90%) and CD14$^+$CD16$^+$ (~10%) sub-populations. The CD14$^+$CD16$^+$ monocytes exhibit more activity (66.4% CD19$^+$CD22$^+$) compared to the more abundant CD14$^{++}$ (31.4%) cells. Even after only 1 h, CD19 and CD22 are specifically reduced from Daudi cells when treated with RFB4 in the presence of PBMCs or purified monocytes. These results demonstrate that CD19 and CD22 are transferred from Daudi cells to both populations of monocytes.

Example 8

RFB4-Induced Trogocytosis with NK Cells

CD19 and CD22 are significantly reduced from Daudi cells in monocyte-depleted PBMCs, suggesting the involvement of effector cells in addition to monocytes. NK cells, which express FcγRIII (CD16), are identified among PBMCs by flow cytometry as CD14-CD16+ cells located in the lymphocyte (forward vs. side scatter) gate. Using Daudi/PBMC and Daudi/monocyte-depleted PBMC mixtures, the lymphocyte gate is further gated for CD14 and CD16 to identify CD14$^-$CD16$^+$ NK cells. NK cells potently acquire CD19 and CD22 when either PBMCs or monocyte-depleted PBMCs are mixed with Daudi and RFB4. These results indicate that NK cells can function in RFB4-induced trogocytosis.

Example 9

RFB4-Induced Trogocytosis with Granulocytes

Granulocytes, or polymorphonuclear cells, which comprise mostly neutrophils, are separated from the PBMCs during processing of whole blood. Granulocytes, which express FcγRIII (CD16), are assessed for their ability to participate in trogocytosis when mixed with Daudi cells and RFB4. Granulocytes are readily gated from the Daudi cells by side scattering and CD16. When mixed with Daudi cells and treated with RFB4, but not the isotype control mAb, granulocytes stain positive for CD22 (30.4% positive), CD19 (40.9% positive) and CD79b (13.7% positive). Following the 1-h incubation, a significant reduction on Daudi of each antigen indicates their transfer from Daudi to granulocytes.

Example 10

Ex Vivo Trogocytosis with SLE Patient PBMCs

PBMCs are isolated from blood specimens of systemic lupus erythematosus (SLE, lupus) patients, who have not received any therapy for their disease (naïve), and treated ex vivo with RFB4, using the same method that is applied to PBMCs from healthy donors. PBMCs of naive SLE patients respond similarly to healthy PBMCs, where CD22, CD19, CD21 and CD79b on the surface of B cells are reduced to 11±4, 53±8, 45±4 and 75±1% control, respectively. Also similar to the results from normal donor PBMCs, $CD27^-$ naive B cells are more responsive than $CD27^+$ memory B cells, and, a $F(ab')_2$ fragment of RFB4 does not induce the reduction of CD19, CD21 or CD79b. PBMCs isolated from blood specimens of SLE patients who currently are on RFB4 immunotherapy have minimal response to ex vivo treatment with RFB4, presumably due to low levels of CD22 on their B cells, resulting from therapy.

Example 11

Administration of hRFB4 in Systemic Lupus Erythematosus (SLE)

An open-label, single-center study of patients with moderately active SLE (total British Isles Lupus Assessment Group (BILAG) score 6 to 12) is conducted. Patients receive dosages of hRFB4 of 50, 100, 200, and 400 mg subcutaneously (SC) every week for 6 weeks. Evaluations include safety, SLE activity (BILAG), blood levels of B and T cells, human anti-RFB4 antibody (HAHA) titers, and levels of cell surface CD19, CD20, CD21, CD22 and CD79b on B cells. It is determined that a dosage of 50-100 mg per SC injection results in optimal depletion of B cell CD19, while producing less than 50% depletion of normal B cells. Subsequently, a subcutaneous dose of 100 mg hRFB4 is administered to a new group of patients with moderately active SLE.

Total BILAG scores decrease by at least 50% in all patients, with 92% having decreases continuing to at least 18 weeks. Almost all patients (93%) experience improvement in at least one BILAG B- or C-level disease activity at 6, 10 and 18 weeks. Additionally, 3 patients with multiple BILAG B involvement at baseline have completely resolved all B-level disease activities by 18 weeks. hRFB4 is well tolerated, with no evidence of immunogenicity or significant changes in T cells, immunoglobulins or autoantibody levels. B-cell levels decrease by an average of 35% at 18 weeks and remain depressed for 6 months post-treatment.

Example 12

Administration of hRFB4 in Rheumatoid Arthritis

Patients who have failed therapy with at least one TNFα inhibitor receive 4 doses of 40, 80, 160 or 320 mg hRFB4 injected s.c. every week or every two weeks. The antibody is either administered alone or in conjunction with oral methotrexate (10-25 mg/week). Occasional mild to moderate transient injection reactions are seen with the s.c. injection and no other safety issues are observed. The s.c. hRFB4 exhibits a slow release pattern over several days. Transient B-cell depletion is observed at all dosage levels of hRFB4. Depletion of B cell surface levels of CD19, CD20, CD21, CD22 and CD79b is observed at a moderate level with 80 mg and at a much higher level at 160 mg hRFB4.

Objective responses are observed at all dose levels of s.c. hRFB4, but with particularly high responses at the dose of 160 mg weekly for six weeks. All serum samples evaluated for human anti-hRFB4 antibody (HAHA) are negative. Six months after treatment, optimal outcome is observed in the group treated with 160 mg hRFB4, with decreased response at either higher or lower dosages. It is concluded that under these conditions, 160 mg hRFB4 is the optimum dosage.

Example 13

Administration of hRFB4 in Sjögren's Syndrome

Patients with primary Sjögren's syndrome receive 8 doses of 20, 40, 80 or 160 mg hRFB4 injected s.c. every week or every two weeks. Occasional mild to moderate transient injection reactions are seen with the s.c. injection and no other safety issues are observed. Transient B-cell depletion is observed at all dosage levels of hRFB4.

Objective responses are observed at all dose levels of s.c. hRFB4, but with particularly high responses at the dose of 80 mg. All serum samples evaluated for human anti-hRFB4 antibody (HAHA) are negative. Six months after treatment, optimal outcome is observed in the group treated with 80 mg hRFB4, with a concommitent decrease in median corticosteroid from 17.5 mg/day to 8.3 mg/day. The study shows good efficacy and tolerance of hRFB4 in patients with pSS and systemic involvement.

Example 14

Administration of hRFB4 in Acute Lymphocytic Leukemia (ALL)

Patients with previously untreated or relapsed ALL receive 4 doses of 10, 20, 40 or 80 mg P2PDox-conjugated hRFB4 injected i.v. every two weeks. Only occasional mild to moderate transient injection reactions are seen and no other safety issues are observed, except for neutropenia, which can be controlled by interrupting therapy until improved or administering a G-CSF leukocyte stimulator, as per conventional practice. Rapid B-cell and ALL ablation is observed at all dosage levels of P2PDox-hRFB4, but more strikingly at the two highest doses given for at least 4 weeks. Objective responses are observed at all dose levels of P2PDox-hRFB4, but with particularly high responses of 30% (mostly partial responses) at the highest dose. All serum samples evaluated for human anti-hRFB4 antibody (HAHA) are negative.

Example 15

Administration of hRFB4 in Follicular NHL

Patients with previously untreated follicular NHL receive 6 to 8 cycles of therapy every 3 weeks, with 200 mg hRFB4 injected s.c., either alone or in combination with CHOP or R-CHOP. Control subjects are administered R-CHOP alone. Premedications consist of intravenous ondansetron 8 mg plus prednisone 100 mg orally for nausea and diphenhydramine 50 mg orally plus acetaminophen 650 mg orally for prevention of hypersensitivity reaction to antibody. The combination of hRFB4 with R-CHOP is found to be more efficacious than either therapy alone, or the combined effect of separate administration.

Occasional mild to moderate transient injection reactions are seen with the s.c. injection of hRFB4 and no other safety issues are observed. Neuropathy is commonly observed with R-CHOP therapy, with 1 patient experiencing grade 3 sensory neuropathy and 2 patients experiencing grade 4 hematologic toxicity. Of evaluable patients treated with the combination of hRFB4 and R-CHOP, 100% respond to therapy, with a complete response rate of 76%.

Example 16

Administration of hRFB4 in Hairy Cell Leukemia

Patients with previously untreated or relapsed hairy cell leukemia receive 4 doses of 40, 80, 160 or 320 mg hRFB4 injected s.c. every week or every two weeks. Occasional mild to moderate transient injection reactions are seen with the s.c. injection and no other safety issues are observed. The s.c. hRFB4 exhibits a slow release pattern over several days. Transient B-cell depletion is observed at all dosage levels of hRFB4. Depletion of B cell surface levels of CD19, CD20, CD21, CD22 and CD79b is observed at a moderate level with 40 mg and at a much higher level at 80 mg hRFB4.

Objective responses are observed at all dose levels of s.c. hRFB4, but with particularly high responses of 30% (mostly partial responses) at the dose of 80 mg. All serum samples evaluated for human anti-hRFB4 antibody (HAHA) are negative. Six months after treatment, optimal outcome is observed in the group treated with 80 mg hRFB4, with decreased response at either higher or lower dosages. It is concluded that under these conditions, 80 mg hRFB4 is the optimum dosage that was used. Monitoring response of BCR levels to therapeutic antibody provides an effective surrogate marker for determining antibody efficacy and is predictive of disease prognosis in response to therapy.

Example 17

Efficacy of hRFB4-SN-38 Conjugate in Human Burkitt Lymphoma Xenografts

Experimental Design.

A humanized anti-human CD22 monoclonal antibody, hRFB4, was conjugated with SN-38 as described in U.S. Pat. Nos. 7,999,083 and 8,080,250 (the Examples section of each of which is incorporated herein by reference) at a drug to antibody ratio of 5.71. This antibody drug conjugate (ADC) was tested in mice bearing subcutaneous (s.c.) Ramos Burkitt lymphoma tumors. Efficacy was compared to another anti-CD22 SN-38-ADC, hLL2-SN-38.

To perform this study, 5 week-old female NCr athymic nu/nu mice were injected s.c. with Ramos cells that were harvested from tissue culture ($1 \times 10^7$ cells per mouse). Once tumors reach approximately 0.2 cm³ in size, they were divided up into treatment groups. Mice received 250 µg hRFB4-SN-38 i.p. twice weekly for two weeks. Likewise, mice received hLL2-SN-38 or a non-tumor targeting anti-CEACAM5 SN-38-ADC (hMN14-SN-38) at the same dose/schedule as the hRFB4-SN-38. Saline control mice received 100 µL i.p. injections twice weekly for two weeks. Treatment groups are summarized in Table 8 below. Tumors were measured and mice weighed twice weekly. Animals were euthanized for disease progression if their tumor volumes exceeded 1.0 cm³ in size.

TABLE 8

In Vivo Efficacy of hRFB4-SN-38 Immunoconjugate Therapeutic Efficacy of hRFB4-SN-38 in Mice Bearing a Human Burkitt Lymphoma Xenograft (Ramos)

| Group | (N) | Amount Injected | Schedule |
| --- | --- | --- | --- |
| 1 | 6 | Saline (100 µL i.p.) | Twice wkly × 2 wks |
| 2 | 5 | hRFB4-SN-38 (250 µg i.p.) | Twice wkly × 2 wks |
| 3 | 6 | hLL2-SN-38 (250 µg i.p.) | Twice wkly × 2 wks |
| 4 | 6 | hMN14-SN-38 (250 µg i.p.) | Twice wkly × 2 wks |

Results.

Survival curves are shown in FIG. 7. Animals were deemed to have died from disease progression if their tumors exceeded 1.0 cm³ in size. As is characteristic with Ramos, the tumors grew very quickly with all the mice in the saline control group dead by day 7 (median survival time (MST)=7 days post-therapy initiation). Likewise, in mice treated with the non-tumor targeting hMN14-SN-38 control, a MST of only 5 days was achieved in this group. In contrast, mice treated with hRFB4-SN-38 resulted in a MST of greater than 87 days which is a significant improvement when compared to both the saline and hMN14-SN-38 control groups (P<0.0024; log-rank test). While the other anti-CD22 ADC (hLL2-SN-38) was significantly better than saline control (P=0.0012) there was no significant difference when compared to hMN14-SN-38 control group of animals. When compared to hLL2-SN-38, hRFB4-SN-38 proved to be superior with 4 of 5 mice tumor free when the study ended on day 87 in comparison to only 1 of 6 mice tumor free in the hLL2-SN-38 treatment group (P=0.0209). Overall, this experiment demonstrated that hRFB4-SN-38 is a potent agent against a very aggressive Burkitt lymphoma and shows surprisingly superior efficacy compared to the hLL2 anti-CD22 antibody.

Example 18

Combination Therapy of SLE with hRFB4 and hLL2

Patients with SLE who have failed at least one previous therapy receive combination therapy with 160 mg each of hRFB4 and hLL2 (epratuzumab), administered s.c. in 2 injections weekly for four weeks. Control groups receive hRFB4 alone, hLL2 alone or irrelevant antibody (hMN-14)

at the same dosage and schedule. Only occasional mild to moderate transient injection reactions are seen and no other safety issues are observed, except for neutropenia, which can be controlled by interrupting therapy until improved or administering a G-CSF leukocyte stimulator, as per conventional practice. Objective responses are observed with hRFB4 alone, hLL2 alone and the combination of hRFB4 and hLL2, but with particularly high responses of 55% (mostly partial responses) with the combination therapy. All serum samples evaluated for anti-human antibodies (HAHA) are negative.

Example 19 hRFB4 Conjugates of Pro-2-Pyrrolinodoxorubicin (P2PDox)

A general scheme for producing an exemplary P2PDox is shown in Scheme 1 below. We have performed 1-g scale reactions to generate >1 g of 4,4-diacetoxybutyraldehyde in an yield of ~40%. To avoid using sodium cyanoborohydride that can potentially contaminate products with cyanide, the reducing agent was changed to sodium triacetoxyborohydride in reductive alkylation. On an exploratory scale, >80% conversion of doxorubicin to P2PDox was recorded. This was increased to 2-g scale to generate >1 g of P2PDox. (Scheme 1). The 4,4-diacetoxybutyraldehyde was prepared by a modification of the reported method (Nagy et al., 1998, Proc Natl Acad Sci USA 95:1794-9), which was necessary to avoid a hazardous ozonolysis step. Diacetoxylation of commercially available 4-pentene-1-al with acetic anhydride and indium chloride catalysis, followed by oxidative cleavage of olefin by ruthenium chloride and sodium periodate combination (Yang & Zhang, 2001, 66:4814-8) furnished the 4,4-diacetoxybutyraldehyde, which was reductively coupled to doxorubicin to obtain P2PDox. The following steps were involved: (i) To a mixture of acetic anhydride (7.45 mL) and indium chloride (0.56 g) in dichloromethane (20 mL) was added 5.05 g of 4-penten-1-al. After 10 to 30 min, the reaction mixture was treated with 25% aqueous sodium acetate (20 mL), and the organic layer was washed with brine and dried. Solvent removal gave 15.3 g of the liquid product, which was taken to the next step; (ii) 3.5 mM ruthenium chloride stock solution in water (69.4 mL) was added to the solution of the step (i) product in dichloromethane in 6:1 acetonitrile-water (350 mL). Sodium periodate (29.7 g) was added in portions. After completion of reaction, as judged by TLC analysis, the reaction mixture was treated with 30 mL of saturated sodium thiosulfate, filtered through a pad of celite, and acetonitrile was evaporated off. The remaining aqueous layer was extracted with ethyl acetate, washed with 25% sodium acetate, water, and brine, and dried. The crude material was purified by chromatography on silica gel using ethyl acetate-hexane mixture for elution. The pure product was used for reductive alkylation of doxorubicin in the next step; (iii) 1.5 grams of doxorubicin hydrochloride was dissolved in 1,1,1,3,3,3-hexafluoroisopropanol (195 mL) and diisopropylethylamine (2.7 mL), and reacted with 3.4 g (7-fold molar excess) of the aldehyde from step (ii) and 0.66 g of sodium triacetoxyborohydride. The reaction was complete in 10 min, and the product was purified on silica gel using methylene chloride-isopropanol mixtures for elution, resulting in 0.96 g of pure product. Electrospray mass spectrum showed the mass at m/z 716.2570 (M+H) consistent with the structure of the product. The structure was also confirmed by proton and C-13 NMR spectra. (iv) P2PDox from step iii was converted to MCC hydrazone using SMCC hydrazide as follows: To 0.6 g of P2PDox dissolved in 75 mL of anhydrous methanol, and treated with 0.34 g of SMCC hydrazide, calculated to be 1.8-fold excess based on the spectrophotometric quantification of the amount of P2PDox used. The percent conversion was judged to be 88% by HPLC. LC-MS analysis the showed the product peak at m/z of 949.3734 (M+H), consistent with the calculated mass (m/z) of 949.3713 (M+H). The material, after solvent removal, was used as such for conjugation since underivatized starting material did not conjugate and was removed during conjugate purification process.

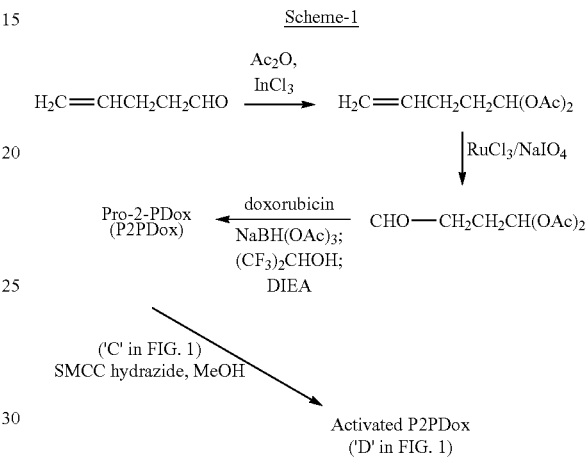

Scheme-1

Small-Scale Conjugate Preparation—

Conjugate preparation followed a general methodology of mildly reducing interchain disulfides of IgG with TCEP in PBS, followed by coupling to a 10-fold excess of activated P2PDox. The conjugates were purified on centrifuged size exclusion chromatography (SEC) on SEPHADEX® equilibrated in 25 mM 3-(N-morpholino)propanesulfonic acid (MOPS), pH 6.8, followed by passage over a hydrophobic column. The products were formulated with trehalose and polysorbate 80, and lyophilized. The conjugated product, with a substitution in the range of 4-7 drug/IgG, eluted as a single peak by size-exclusion HPLC, and contained typically <1% of unconjugated free drug by reversed-phase HPLC.

Scaled-Up Conjugate Preparation

Conjugate of humanized anti-TROP-2 antibody, hRS7, was prepared, on 5-g and 10-g scale, by TCEP reduction of an antibody, followed by in situ conjugation using a 12-fold excess of activated P2PDox, with DMSO as co-solvent (5% v/v). The product was purified by tangential flow filtration using 25 mM MOPS buffer, pH 6.8, with 20-diafiltration volumes for purification. The product was formulated with 25 mM trehalose and 0.01% TWEEN® 80, aliquotted in 20-mg or 100-mg lots, and lyophilized.

Representative Conjugates

|   | Conjugate | Lot | % Protein recover | P2PDox/ IgG | HPLC Aggr. | Free drug |
|---|---|---|---|---|---|---|
| 1 | hIMMU-31-P2PDox | II22-138 | 75.0% | 7.39 | 1.9% | 0.26% |
| 2 | hA20-P2PDox | II22-135 | 85.7% | 6.79 | <2% | <0.1% |
| 3 | hLL1-P2PDox | II22-145 | 88.6% | 7.10 | 2.8% | 0.2% |

|   | Conjugate | Lot | % Protein recover | P2PDox/ IgG | HPLC Aggr. | Free drug |
|---|-----------|-----|-------------------|-------------|------------|-----------|
| 4 | hRS7-P2PDox | II22-142 | 80.1% | 7.17 | 1.8% | 0.12% |
| 5 | hMN15-P2PDox | II22-180 | 74.9% | 6.87 | 1.1% | 0.46% |
| 6 | hMN-14-P2PDox | II22-183 | 80.2% | 6.78 | 2.1% | 0.53% |

Conjugates have also been prepared for hPAM4-P2PDox, hLL2-P2PDox and RFB4-P2PDox, with similar protein recovery and purity (not shown).

All patents and other references cited in the specification are indicative of the level of skill of those skilled in the art to which the invention pertains, and are incorporated herein by reference, including any Tables and Figures, to the same extent as if each reference had been incorporated by reference individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the invention.

What is claimed is:

1. A humanized anti-CD22 antibody or antigen-binding fragment thereof comprising heavy chain complementarity determining region (CDR) sequences CDR1 (IYDMS, SEQ ID NO:1), CDR2 (YISSGGGTTYYPDTVKG, SEQ ID NO:2) and CDR3 (HSGYGSSYGVLFAY, SEQ ID NO:3), light chain CDR sequences CDR1 (RASQDISNYLN, SEQ ID NO:4), CDR2 (YTSILHS, SEQ ID NO:5) and CDR3 (QQGNTLPWT, SEQ ID NO:6), heavy chain framework region (FR) amino acid residues Q1, V5, F27, S30, V48, A49, R67, F68, R98, T117 and L118, and light chain residues L4, I21, S22, K39, Y71, G100, V104, and K107, using Kabat numbering.

2. The anti-CD22 antibody or fragment thereof of claim 1, further comprising heavy chain framework region (FR) amino acid residues Q6, A9, E10, V11, K12, K13, S16, V18, K19, V20, K23, T28, Q43, T71, A72, E74, S75, T76, T78, A79, M81, E82, L83, S84, S88, F93, and F95, and light chain residues D70, F73, I83, Y87, and Q105, using Kabat numbering.

3. The anti-CD22 antibody or fragment thereof of claim 1, wherein the antibody or fragment thereof is capable of reducing the levels of one or more proteins on the surface of B cells selected from the group consisting of CD19, CD20, CD21, CD22 and CD79b.

4. The anti-CD22 antibody fragment of claim 1, wherein the antibody fragment is selected from the group consisting of a F(ab')2, F(ab)2, Fab', Fab, Fv, scFv, single domain antibody (VHH), diabody, and half-molecule of IgG4.

5. The anti-CD22 antibody or fragment thereof of claim 1, wherein the antibody or fragment thereof is not an scFv antibody fragment.

6. The anti-CD22 antibody or fragment thereof of claim 5, wherein the antibody or fragment thereof is an intact IgG antibody.

7. The anti-CD22 antibody or fragment thereof of claim 1, wherein the anti-CD22 antibody or fragment thereof is part of a bispecific antibody.

8. The anti-CD22 antibody or fragment thereof of claim 7, wherein the bispecific antibody is a DNL complex.

9. The anti-CD22 antibody or fragment thereof of claim 7, wherein the bispecific antibody binds to (i) B cells, or (ii) both B cells and T cells.

10. The anti-CD22 antibody or fragment thereof of claim 7, wherein the bispecific antibody binds to a hapten.

11. The anti-CD22 antibody or fragment thereof of claim 10, wherein the hapten is In-DTPA or HSG.

12. The anti-CD22 antibody or fragment thereof of claim 7, wherein the bispecific antibody binds to CD22 and to an antigen selected from the group consisting of carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD47, CD52, CD54, CD55, CD59, CD64, CD66a-e, CD67, CD70, CD70L, CD74, CD79a, CD80, CD83, CD95, CD126, CD133, CD138, CD147, CD154, CXCR4, AFP, PSMA, CEACAM5, CEACAM-6, c-MET, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-23, IL-25, IP-10, MAGE, mCRP, MCP-1, MIP-1A, MIP-1B, MIF, MUC1, MUC2, MUC3, MUC4, MUC5, MUC5a,c, MUC16, PAM4 antigen, NCA-95, NCA-90, Ia, HM1.24, EGP-1 (also known as TROP-2), EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, and an oncogene product.

13. The anti-CD22 antibody or fragment thereof of claim 7, wherein the bispecific antibody binds to CD22 and to an antigen selected from the group consisting of BCL-1, BCL-2, BCL-6, CD1a, CD2, CD3, CD4, CD5, CD7, CD8, CD10, CD11 b, CD11c, CD13, CD14, CD15, CD16, CD19, CD20, CD21, CD22, CD23, CD25, CD33, CD34, CD38, CD40, CD40L, CD41a, CD43, CD45, CD47, CD55, CD56, CCD57, CD59, CD64, CD71, CD79a, CD79b, CD117, CD138, CXCR4, FMC-7 and HLA-DR.

14. The anti-CD22 antibody or fragment thereof of claim 1, wherein the anti-CD22 antibody or fragment thereof is not conjugated to any therapeutic or diagnostic agent.

15. The anti-CD22 antibody or fragment thereof of claim 1, wherein the anti-CD22 antibody or fragment thereof is conjugated to at least one therapeutic or diagnostic agent.

16. The anti-CD22 antibody or fragment thereof of claim 15, wherein the therapeutic agent is selected from the group consisting of a radionuclide, an immunomodulator, an anti-angiogenic agent, a pro-apoptotic agent, a cytokine, a chemokine, a drug, a toxin, a hormone, an siRNA and an enzyme.

17. The anti-CD22 antibody or fragment thereof of claim 16, wherein the drug is selected from the group consisting of 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celecoxib, chlorambucil, cisplatinum, Cox-2 inhibitors, CPT-11 SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), pro-2P-DOX, cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, paclitaxel, temazolomide, transplatinum, thalidomide, thioguanine, thiotepa, teniposide, topotecan, uracil mustard, vinorelbine, vinblastine, vincristine, a vinca alkaloid, a tyrophostin, canertinib, dasatinib, erlotinib, gefitinib, imatinib, lapatinib, leflunomide, nilotinib, pazopanib, semaxinib, sorafenib, sunitinib, sutent, vatalanib, PCI-32765 (ibrutinib), PCI-45292, GDC-0834, LFM-A13 and RN486.

18. The anti-CD22 antibody or fragment thereof of claim 16, wherein the toxin is selected from the group consisting of ricin, abrin, alpha toxin, saporin, ribonuclease (RNase), DNase I, *Staphylococcal* enterotoxin-A, pokeweed antiviral protein, gelonin, diphtheria toxin, *Pseudomonas* exotoxin, and *Pseudomonas* endotoxin.

19. The anti-CD22 antibody or fragment thereof of claim 16, wherein the therapeutic agent is an immunomodulator selected from the group consisting of a cytokine, a stem cell growth factor, a lymphotoxin, a hematopoietic factor, a colony stimulating factor (CSF), an interleukin (IL), erythropoietin, thrombopoietin, tumor necrosis factor (TNF), granulocyte-colony stimulating factor (G-CSF), granulocyte macrophage-colony stimulating factor (GM-CSF), interferon-α, interferon-α, interferon-γ, interferon-λ, TGF-α, TGF-β, interleukin-1 (IL-1), IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-23, IL-25, LIF, FLT-3, angiostatin, thrombospondin, endostatin and lymphotoxin.

20. The anti-CD22 antibody or fragment thereof of claim 16, wherein the radionuclide is selected from the group consisting of 111In, 111At, 177Lu, 211Bi, 212Bi, 213Bi, 211At, 62Cu, 67Cu, 90Y, 125I, 131I, 133I, 32P, 33P, 47Sc, 111Ag, 67Ga, 153Sm, 161Tb, 152Dy, 166Dy, 161Ho, 166Ho, 186Re, 188Re, 189Re, 211Pb, 212Pb, 223Ra, 225Ac, 227Th, 77As, 89Sr, 99Mo, 105Rh, 149Pm, 169Er, 194Ir, 58Co, 80mBr, 99mTc, 103mRh, 109Pt, 119Sb, 125I, 189mOs, 192Ir, 219Rn, 215Po, 221Fr, 255Fm, 11C, 13N, 15O, 75Br, 198Au, 199Au, 224Ac, 77Br, 113mIn, 95Ru, 97Ru, 103Ru, 105Ru, 107Hg, 203Hg, 121mTe, 122mTe, 227Th, 125mTe, 165Tm, 167Tm, 168Tm, 197Pt, 109Pd, 142Pr, 143Pr, 161Tb, 57Co, 58Co, 51Cr, 59Fe, 75Se, 201Tl, 76Br and 169Yb.

21. The anti-CD22 antibody or fragment thereof of claim 15, wherein the diagnostic agent is selected from the group consisting of a radionuclide, a contrast agent, a fluorescent agent, a chemiluminescent agent, a bioluminescent agent, a paramagnetic ion, an enzyme and a photoactive diagnostic agent.

22. The anti-CD22 antibody or fragment thereof of claim 21, wherein the diagnostic agent is a radionuclide selected from the group consisting of 110In, 111In, 177Lu, 18F, 52Fe, 62Cu, 64Cu, 67Cu, 67Ga, 68Ga, 86Y, 90Y, 89Zr, 94mTc, 94Tc, 99mTc, 120I, 123I, 124I, 125I, 131I, 154-158Gd, 32F, 11C, 13N, 15O, 186Re, 188Re, 51Mn, 52mMn, 55Co, 72As, 75Br, 76Br, 82mRb, 83Sr, or other gamma-, beta-, or positron-emitters.

23. The anti-CD22 antibody or fragment thereof of claim 21, wherein the paramagnetic ion is selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

24. The anti-CD22 antibody or fragment thereof of claim 21, wherein the diagnostic agent is a fluorescent labeling compound selected from the group consisting of fluorescein isothiocyanate, rhodamine, phycoerytherin, phycocyanin, allophycocyanin, o-phthaldehyde and fluorescamine, or a chemiluminescent labeling compound selected from the group consisting of luminol, isoluminol, an aromatic acridinium ester, an imidazole, an acridinium salt and an oxalate ester, or a bioluminescent compound selected from the group consisting of luciferin, luciferase and aequorin.

25. A composition comprising an anti-CD22 antibody or fragment thereof of according to claim 1.

* * * * *

SEQUENCE LISTING

```
<160> NUMBER OF SEQ ID NOS: 145

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Tyr Asp Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Ile Ser Ser Gly Gly Gly Thr Thr Tyr Tyr Pro Asp Thr Val Lys
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Ser Gly Tyr Gly Ser Ser Tyr Gly Val Leu Phe Ala Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Asp Ile Ser Asn Tyr Leu Asn
1               5                   10
```

```
<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Thr Ser Ile Leu His Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Gly Asn Thr Leu Pro Trp Thr
1               5

<210> SEQ ID NO 7
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Ile Tyr
            20                  25                  30

Asp Met Ser Trp Val Arg Gln Ala Pro Gly Gln Gly Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
        115                 120

<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Leu Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30
```

Leu Asn Trp Tyr Gln Gln Lys Pro Gly Lys Ala Pro Lys Leu Leu Ile
            35                  40                  45

Tyr Tyr Thr Ser Ile Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Val Gln Ile Lys Arg
            100                 105

<210> SEQ ID NO 9
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Pro Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Ser
            20                  25                  30

Ala Ile Ile Trp Val Arg Gln Ala Pro Gly Gln Gly Leu Glu Trp Met
        35                  40                  45

Gly Gly Ile Val Pro Met Phe Gly Pro Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Gly Gly Tyr Gly Ile Tyr Ser Pro Glu
            100                 105

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Ala Glu Leu Ser Lys Pro Gly Ala
1               5                   10                  15

Ser Val Lys Met Ser Cys Lys Ala Ser Gly Tyr Thr Phe Thr Ser Tyr
            20                  25                  30

Trp Leu His Trp Ile Lys Gln Arg Pro Gly Gln Gly Leu Glu Trp Ile
        35                  40                  45

Gly Tyr Ile Tyr Pro Arg Asn Asp Tyr Thr Glu Tyr Asn Gln Asn Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Asp Ile Thr Thr Phe Tyr Trp Gly Gln Gly Thr Thr Leu
            100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Leu His Trp Val Arg Gln Ala Pro Gly Gln Gly Leu Glu Trp Ile
        35                  40                  45

Gly Tyr Ile Tyr Pro Arg Asn Asp Tyr Thr Glu Tyr Asn Gln Asn Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Arg Asp Ile Thr Thr Phe Tyr Trp Gly Gln Gly Thr Thr Val
            100                 105                 110

Thr Val Ser Ser
        115

<210> SEQ ID NO 12
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ala
        115                 120

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

```
Trp Gly Gln Gly Thr Leu Val Thr Val Ser Ser
1               5                   10
```

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                  30

Leu Asn Trp Tyr Gln Gln Thr Pro Gly Lys Ala Pro Lys Leu Leu Ile
        35                  40                  45

Tyr Glu Ala Ser Asn Leu Gln Ala Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Gln Ser Leu Pro Tyr
                85                  90                  95

Thr Phe Gly Gln Gly Thr Lys Leu Gln Ile Thr Arg
            100                 105
```

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Asp Ile Gln Leu Thr Gln Ser Pro Ser Ser Leu Ala Val Ser Ala Gly
1               5                   10                  15

Glu Asn Val Thr Met Ser Cys Lys Ser Ser Gln Ser Val Leu Tyr Ser
            20                  25                  30

Ala Asn His Lys Asn Tyr Leu Ala Trp Phe Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Arg Val Gln Val Glu Asp Leu Ala Ile Tyr Tyr Cys His Gln
                85                  90                  95

Tyr Leu Ser Ser Trp Thr Phe Gly Gly Gly Thr Lys Leu Glu Ile Lys
            100                 105                 110

Arg
```

```
<210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Leu Thr Gln Ser Pro Ser Ser Leu Ser Ala Ser Val Gly
1               5                   10                  15

Asp Arg Val Thr Met Ser Cys Lys Ser Gln Ser Val Leu Tyr Ser
            20                  25                  30

Ala Asn His Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gly Gly Thr Lys Val Gln Ile Lys
            100                 105                 110

Arg

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Leu Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 18
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 18

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 19
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 20

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 21
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ile Glu Tyr Leu Ala Lys Gln Ile Val Asp Asn Ala Ile Gln Gln
1               5                   10                  15

Ala

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 24
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 24

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Lys Glu Glu
        35                  40                  45

Ala Lys
    50

<210> SEQ ID NO 25
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 26
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 27
<211> LENGTH: 51
<212> TYPE: PRT
<213> ORGANISM: Homo sapiens

<400> SEQUENCE: 27

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 28
<211> LENGTH: 54
<212> TYPE: PRT
<213> ORGANISM: Homo sapiens
```

```
<400> SEQUENCE: 28

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
                20                  25                  30

Pro Met Lys Phe Leu Arg Glu His Phe Glu Lys Leu Glu Lys Glu Glu
            35                  40                  45

Asn Arg Gln Ile Leu Ala
        50

<210> SEQ ID NO 29
<211> LENGTH: 44
<212> TYPE: PRT
<213> ORGANISM: Homo sapiens

<400> SEQUENCE: 29

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
                20                  25                  30

Glu Tyr Phe Thr Arg Leu Arg Glu Ala Arg Arg Gln
            35                  40

<210> SEQ ID NO 30
<211> LENGTH: 44
<212> TYPE: PRT
<213> ORGANISM: Homo sapiens

<400> SEQUENCE: 30

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Gly Phe Ala Leu
                20                  25                  30

Gln His Phe Thr Arg Leu Gln Gln Glu Asn Glu Arg
            35                  40

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (10)..(10)
<223> OTHER INFORMATION: Thr or Ser
```

```
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val
```

-continued

```
<400> SEQUENCE: 31

Xaa Xaa Ile Xaa Ile Pro Pro Xaa Leu Xaa Xaa Leu Leu Xaa Xaa Tyr
1               5                   10                  15

Xaa Val Xaa Val Leu Xaa Xaa Xaa Pro Pro Xaa Leu Val Xaa Phe Xaa
            20                  25                  30

Val Xaa Tyr Phe Xaa Xaa Leu Xaa Xaa Xaa Xaa
        35                  40

<210> SEQ ID NO 32
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 33
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 34
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 35
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 35

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 36
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 37
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 38
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 39
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 39

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 40
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 41
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 42
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 43
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 43

Ser His Ile Gln Ile Pro Pro Gly Leu Thr Glu Leu Leu Gln Gly Tyr
1               5                   10                  15

Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 44
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser His Ile Gln Ile Pro Pro Gly Leu Thr Glu Leu Leu Gln Gly Tyr
1               5                   10                  15

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 45
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ser His Ile Gln Ile Pro Pro Gly Leu Thr Glu Leu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala
        35                  40

<210> SEQ ID NO 46
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ser His Ile Gln Ile Pro Pro Gly Leu Thr Glu Leu Leu Gln Gly Tyr
1               5                   10                  15

Thr Val Glu Val Leu Arg Gln Gln Pro Pro Glu Leu Val Glu Phe Ala
            20                  25                  30

Val Glu Tyr Phe Thr Arg Leu Arg Glu Ala Arg Ala
        35                  40

<210> SEQ ID NO 47
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 47

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Asp Phe Ala
            20                  25                  30

Val Glu Tyr Phe Thr Arg Leu Arg Glu Ala Arg Ala
        35                  40

<210> SEQ ID NO 48
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Leu
            20                  25                  30

Val Glu Tyr Phe Thr Arg Leu Arg Glu Ala Arg Ala
        35                  40

<210> SEQ ID NO 49
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
            20                  25                  30

Val Glu Tyr Phe Thr Arg Leu Arg Glu Ala Arg Ala
        35                  40

<210> SEQ ID NO 50
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
            20                  25                  30

Val Glu Tyr Phe Thr Arg Leu Arg Glu Ala Arg Ala
        35                  40

<210> SEQ ID NO 51
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 51

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Asp Tyr Phe Thr Arg Leu Arg Glu Ala Arg Ala
        35                  40

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asn Ile Glu Tyr Leu Ala Lys Gln Ile Val Asp Asn Ala Ile Gln Gln
1               5                   10                  15

Ala

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Leu Glu Tyr Leu Ala Lys Gln Ile Val Asp Asn Ala Ile Gln Gln
1               5                   10                  15

Ala

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Val Glu Tyr Leu Ala Lys Gln Ile Val Asp Asn Ala Ile Gln Gln
1               5                   10                  15

Ala

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Ile Asp Tyr Leu Ala Lys Gln Ile Val Asp Asn Ala Ile Gln Gln
1               5                   10                  15

Ala
```

```
<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Ile Glu Phe Leu Ala Lys Gln Ile Val Asp Asn Ala Ile Gln Gln
1               5                   10                  15

Ala

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Ile Glu Thr Leu Ala Lys Gln Ile Val Asp Asn Ala Ile Gln Gln
1               5                   10                  15

Ala

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Ile Glu Ser Leu Ala Lys Gln Ile Val Asp Asn Ala Ile Gln Gln
1               5                   10                  15

Ala

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Ile Glu Tyr Ile Ala Lys Gln Ile Val Asp Asn Ala Ile Gln Gln
1               5                   10                  15

Ala

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Ile Glu Tyr Val Ala Lys Gln Ile Val Asp Asn Ala Ile Gln Gln
1               5                   10                  15

Ala
```

```
<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Ile Glu Tyr Leu Ala Arg Gln Ile Val Asp Asn Ala Ile Gln Gln
1               5                   10                  15

Ala

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ile Glu Tyr Leu Ala Lys Asn Ile Val Asp Asn Ala Ile Gln Gln
1               5                   10                  15

Ala

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ile Glu Tyr Leu Ala Lys Gln Ile Val Glu Asn Ala Ile Gln Gln
1               5                   10                  15

Ala

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Ile Glu Tyr Leu Ala Lys Gln Ile Val Asp Gln Ala Ile Gln Gln
1               5                   10                  15

Ala

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Ile Glu Tyr Leu Ala Lys Gln Ile Val Asp Asn Ala Ile Asn Gln
1               5                   10                  15

Ala
```

```
<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Ile Glu Tyr Leu Ala Lys Gln Ile Val Asp Asn Ala Ile Gln Asn
1               5                   10                  15

Ala

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ile Glu Tyr Leu Ala Lys Gln Ile Val Asp Asn Ala Ile Gln Gln
1               5                   10                  15

Leu

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Ile Glu Tyr Leu Ala Lys Gln Ile Val Asp Asn Ala Ile Gln Gln
1               5                   10                  15

Ile

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Ile Glu Tyr Leu Ala Lys Gln Ile Val Asp Asn Ala Ile Gln Gln
1               5                   10                  15

Val

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
```

```
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile or Val

<400> SEQUENCE: 70

Xaa Xaa Xaa Xaa Xaa Ala Xaa Xaa Ile Val Xaa Xaa Ala Ile Xaa Xaa
1               5                   10                  15

Xaa

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Ile Glu Tyr Val Ala Lys Gln Ile Val Asp Tyr Ala Ile His Gln
1               5                   10                  15

Ala

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Ile Glu Tyr Lys Ala Lys Gln Ile Val Asp His Ala Ile His Gln
1               5                   10                  15

Ala
```

```
<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Ile Glu Tyr His Ala Lys Gln Ile Val Asp His Ala Ile His Gln
1               5                   10                  15

Ala

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Ile Glu Tyr Val Ala Lys Gln Ile Val Asp His Ala Ile His Gln
1               5                   10                  15

Ala

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Pro Leu Glu Tyr Gln Ala Gly Leu Leu Val Gln Asn Ala Ile Gln Gln
1               5                   10                  15

Ala Ile

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Leu Ile Glu Thr Ala Ser Ser Leu Val Lys Asn Ala Ile Gln Leu
1               5                   10                  15

Ser Ile
```

```
<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Ile Glu Glu Ala Ala Ser Arg Ile Val Asp Ala Val Ile Glu Gln
1               5                   10                  15

Val Lys

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Leu Tyr Gln Phe Ala Asp Arg Phe Ser Glu Leu Val Ile Ser Glu
1               5                   10                  15

Ala Leu

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Glu Gln Val Ala Asn Gln Leu Ala Asp Gln Ile Ile Lys Glu Ala
1               5                   10                  15

Thr

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe Glu Glu Leu Ala Trp Lys Ile Ala Lys Met Ile Trp Ser Asp Val
1               5                   10                  15

Phe

<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Leu Val Arg Leu Ser Lys Arg Leu Val Glu Asn Ala Val Leu Lys
1               5                   10                  15

Ala Val
```

```
<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Ala Glu Glu Val Ser Ala Arg Ile Val Gln Val Val Thr Ala Glu
1               5                   10                  15

Ala Val

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Ile Lys Gln Ala Ala Phe Gln Leu Ile Ser Gln Val Ile Leu Glu
1               5                   10                  15

Ala Thr

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Ala Trp Lys Ile Ala Lys Met Ile Val Ser Asp Val Met Gln Gln
1               5                   10                  15

<210> SEQ ID NO 86
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Glu Gln Tyr Ala Asn Gln Leu Ala Asp Gln Ile Ile Lys Glu Ala
1               5                   10                  15

Thr Glu
```

```
<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Phe Glu Glu Leu Ala Trp Lys Ile Ala Lys Met Ile Trp Ser Asp Val
1               5                   10                  15

Phe Gln Gln Cys
            20

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Ile Glu Tyr Leu Ala Lys Gln Ile Pro Asp Asn Ala Ile Gln Gln
1               5                   10                  15

Ala

<210> SEQ ID NO 90
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 91
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 92
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 92

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 93
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 94
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 95
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 96
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25
```

```
<210> SEQ ID NO 97
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 98
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 99
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 100
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 101

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 102
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 103
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 104
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 105
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25
```

```
<210> SEQ ID NO 106

<400> SEQUENCE: 106

000

<210> SEQ ID NO 107
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 107

Xaa His Ile Xaa Ile Pro Pro Gly Leu Xaa Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
            35                  40

<210> SEQ ID NO 108
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DOTA-Phe
<220> FEATURE:
<221> NAME/KEY: MOD_RES
<222> LOCATION: (2)..(2)
<223> OTHER INFORMATION: Lys(HSG)
<220> FEATURE:
<221> NAME/KEY: MOD_RES
<222> LOCATION: (4)..(4)
<223> OTHER INFORMATION: Lys(HSG)-NH2

<400> SEQUENCE: 108

Phe Lys Tyr Lys
1

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aatgcggcgg tggtgacagt a                                           21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aagctcagca cacagaaaga c                                           21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
uaaaaucuuc cugcccacct t                                           21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
ggaagcuguu ggcugaaaat t                                           21
```

```
<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
aagaccagcc ucuuugccca g                                              21

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggaccaggca gaaaacgag                                                 19

<210> SEQ ID NO 115
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
cuaucaggau gacgcgg                                                   17

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
ugacacaggc aggcuugacu u                                              21

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ggtgaagaag ggcgtccaa                                                 19

<210> SEQ ID NO 118
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gatccgttgg agctgttggc gtagttcaag agactcgcca acagctccaa cttttggaaa    60
```

```
<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
aggtggtgtt aacagcagag                                                    20

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
aaggtggagc aagcggtgga g                                                  21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
aaggagttga aggccgacaa a                                                  21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
uauggagcug cagaggaugt t                                                  21

<210> SEQ ID NO 123
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tttgaatatc tgtgctgaga acacagttct cagcacagat attcttttt                    49

<210> SEQ ID NO 124
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
aatgagaaaa gcaaaaggtg ccctgtctc                                          29
```

```
<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
aaucaucauc aagaaagggc a                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
augacuguca ggauguugct t                                              21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gaacgaaucc ugaagacauc u                                              21

<210> SEQ ID NO 128
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
aagcctggct acagcaatat gcctgtctc                                      29

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
ugaccaucac cgaguuuaut t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 130
aagtcggacg caacagagaa a                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
cuaccuuucu acggacgugt t                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ctgcctaagg cggatttgaa t                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
ttauuccuuc uucgggaagu c                                              21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
aaccttctgg aacccgccca c                                              21

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gagcatcttc gagcaagaa                                                 19
```

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136
catgtggcac cgtttgcct                                            19

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
aactaccaga aaggtatacc t                                         21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 138
ucacaguguc cuuuauguat t                                         21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 139
gcaugaaccg gaggcccaut t                                         21

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
ccggacagtt ccatgtata                                            19

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Ala Cys Ser Ser Ser Pro Ser Lys His Cys Gly
1               5                   10

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Phe Cys Ile Gly Arg Leu Cys Gly
1               5

<210> SEQ ID NO 143
<211> LENGTH: 12
<212> TYPE: PRT
<213> ORGANISM: Human immunodeficiency virus

<400> SEQUENCE: 143

Gly Arg Lys Lys Arg Arg Asn Arg Arg Arg Cys Gly
1               5                   10

<210> SEQ ID NO 144
<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
tctagacaca ggacctcacc atgggatgga gctgtatcat cctcttcttg gtagcaacag      60
ctacaggtaa ggggctcaca gtagcaggct tgaggtctgg acatatatat gggtgacaat    120
gacatccact ttgcctttct ctccacaggt gtccactccg acatccagct gacccagtct    180
ccatcatctc tgagcgcatc tgttggagat agggtcacta ttagctgtcg agcaagtcag    240
gacattagca attatctgaa ctggtaccag cagaaaccag ggaaagcacc taaactgctg    300
atctactaca catcaatatt acactccggt gtcccttcgc gattctctgg cagcggatct    360
gggacagatt atactttcac catcagctct cttcaaccag aagacattgc aacatattat    420
tgtcaacagg gtaatacgct tccgtggacg ttcggtggag gaccaaggt gcagatcaaa     480 cgtgagtaga atttaaactt tgcttcctca gttggatcc                          519

<210> SEQ ID NO 145
<211> LENGTH: 672
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
ctcgagcaca caggacctca ccatgggatg gagctgtatc atcctcttct tggtagcaac     60
agctacaggt aagggctca cagtagcagg cttgaggtct ggacatatat atgggtgaca    120
atgacatcca ctttgccttt ctctccacag gtgtccactc ccaggtccag ctggtccaat    180
caggggctga agtcaagaaa cctggggtcat cagtgaaggt ctcctgcaag gcttctggct    240
tcacctttag tatctatgac atgtcttggg tcaggcaggc acctggacag ggtctggaat    300

| | | | | |
|---|---|---|---|---|
| gggtcgcata | cattagtagt | ggtggtggta | ccacctacta | tccagacact gtgaagggcc | 360 |
| gattcacaat | aactgcagac | gaatccacca | atacagccta | catggagctg agcagcctga | 420 |
| ggtctgagga | cacggcattt | tattttgtg | caagacatag | tggctacggt agtagctacg | 480 |
| gggttttgtt | tgcttactgg | ggccaaggca | ccctggtcac | cgtctcctca ggtgagtcct | 540 |
| tacaacctct | ctcttctatt | cagcttaaat | agattttact | gcatttgttg gggggggaaat | 600 |
| gtgtgtatct | gaatttcagg | tcatgaagga | ctagggacac | cttgggagtc agaaagggtc | 660 |
| attgggaagc | tt | | | | 672 |